United States Patent
Yavorsky et al.

(10) Patent No.: US 10,828,419 B2
(45) Date of Patent: Nov. 10, 2020

(54) INFUSION SET WITH PIVOTING METAL CANNULA AND STRAIN RELIEF

(71) Applicant: MEDTRONIC MINIMED, INC., Northridge, CA (US)

(72) Inventors: Matthew William Yavorsky, Granada Hills, CA (US); R. Marie Tieck, Los Angeles, CA (US); Dhivya Sridhar, Pasadena, CA (US); Guangping Zhang, Calabasas, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 135 days.

(21) Appl. No.: 16/121,446

(22) Filed: Sep. 4, 2018

(65) Prior Publication Data

US 2020/0069871 A1 Mar. 5, 2020

(51) Int. Cl.
*A61M 5/158* (2006.01)

(52) U.S. Cl.
CPC .................................. *A61M 5/158* (2013.01)

(58) Field of Classification Search
CPC .. A61M 5/14248; A61M 5/158; A61M 5/162; A61M 2005/1587; A61M 2005/1586
See application file for complete search history.

(56) References Cited

U.S. PATENT DOCUMENTS

| 4,562,751 A | 1/1986 | Nason et al. |
|---|---|---|
| 4,678,408 A | 7/1987 | Nason et al. |
| 4,685,903 A | 8/1987 | Cable et al. |
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |

(Continued)

FOREIGN PATENT DOCUMENTS

WO WO2006015507 A2 2/2006

*Primary Examiner* — Laura A Bouchelle
(74) *Attorney, Agent, or Firm* — Lorenz & Kopf, LLP

(57) ABSTRACT

An infusion set for use with a fluid infusion device having a fluid reservoir includes a cannula that provides a fluid flow path and a first housing. The first housing includes an articulation member coupled to the cannula. The articulation member is pivotable relative to the first housing to move the cannula relative to the first housing. The first housing is coupled to a fluid supply line to provide a fluid to the cannula, and the fluid supply line is to be coupled to the fluid reservoir to receive the fluid. The infusion set includes a second housing uncoupled from the first housing that surrounds the first housing and receives a portion of the fluid supply line.

16 Claims, 28 Drawing Sheets

(56) References Cited

U.S. PATENT DOCUMENTS

| | | | |
|---|---|---|---|
| 6,355,021 B1 | 3/2002 | Nielsen et al. | |
| 6,379,301 B1 | 4/2002 | Worthington et al. | |
| 6,485,465 B2 | 11/2002 | Moberg et al. | |
| 6,544,212 B2 | 4/2003 | Galley et al. | |
| 6,554,798 B1 | 4/2003 | Mann et al. | |
| 6,558,351 B1 | 5/2003 | Steil et al. | |
| 6,572,586 B1 * | 6/2003 | Wojcik | A61M 5/158 128/DIG. 6 |
| 6,591,876 B2 | 7/2003 | Safabash | |
| 6,641,533 B2 | 11/2003 | Causey, III et al. | |
| 6,659,980 B2 | 12/2003 | Moberg et al. | |
| 6,736,797 B1 | 5/2004 | Larsen et al. | |
| 6,749,587 B2 | 6/2004 | Flaherty | |
| 6,752,787 B1 | 6/2004 | Causey, III et al. | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,817,990 B2 | 11/2004 | Yap et al. | |
| 6,932,584 B2 | 8/2005 | Gray et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,454,251 B2 * | 11/2008 | Rezai | 607/115 |
| 7,602,310 B2 | 10/2009 | Mann et al. | |
| 7,621,893 B2 | 11/2009 | Moberg et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,905,868 B2 | 3/2011 | Moberg et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,551,047 B2 * | 10/2013 | Burns | A61M 5/31526 604/167.02 |
| 8,814,831 B2 | 8/2014 | Constantineau et al. | |
| 2004/0122380 A1 * | 6/2004 | Utterberg | A61M 5/3286 604/272 |
| 2007/0123819 A1 | 5/2007 | Mernoe et al. | |
| 2008/0208139 A1 | 8/2008 | Scheurer et al. | |
| 2008/0269687 A1 | 10/2008 | Chong et al. | |
| 2009/0299290 A1 | 12/2009 | Moberg | |
| 2010/0140125 A1 | 6/2010 | Mathiasen et al. | |
| 2010/0160861 A1 | 6/2010 | Causey, III et al. | |
| 2011/0313357 A1 * | 12/2011 | Skutnik | A61M 5/158 604/151 |
| 2012/0265166 A1 * | 10/2012 | Yodfat | A61M 5/1413 604/506 |
| 2016/0303315 A1 | 10/2016 | Momose | |

* cited by examiner

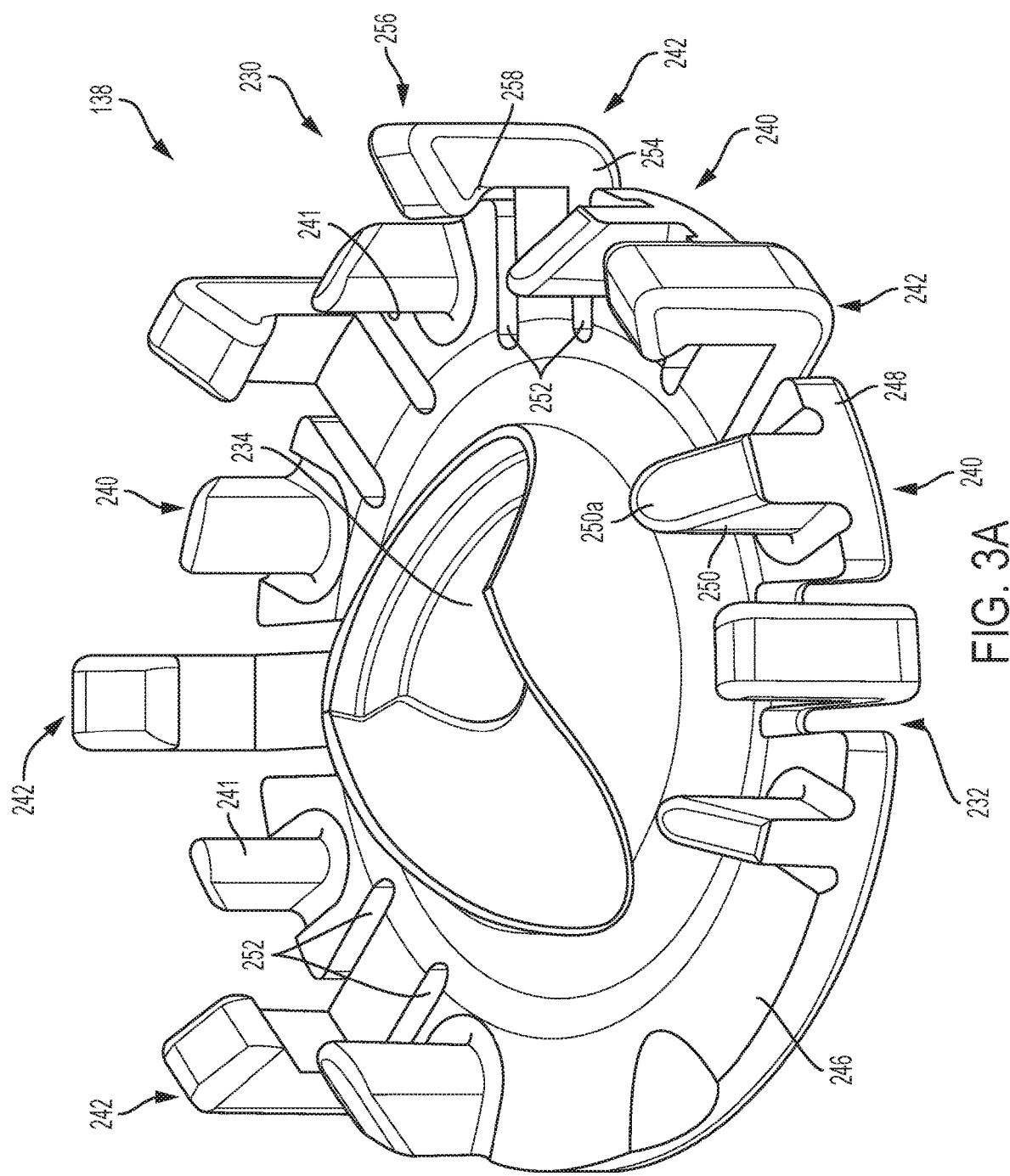

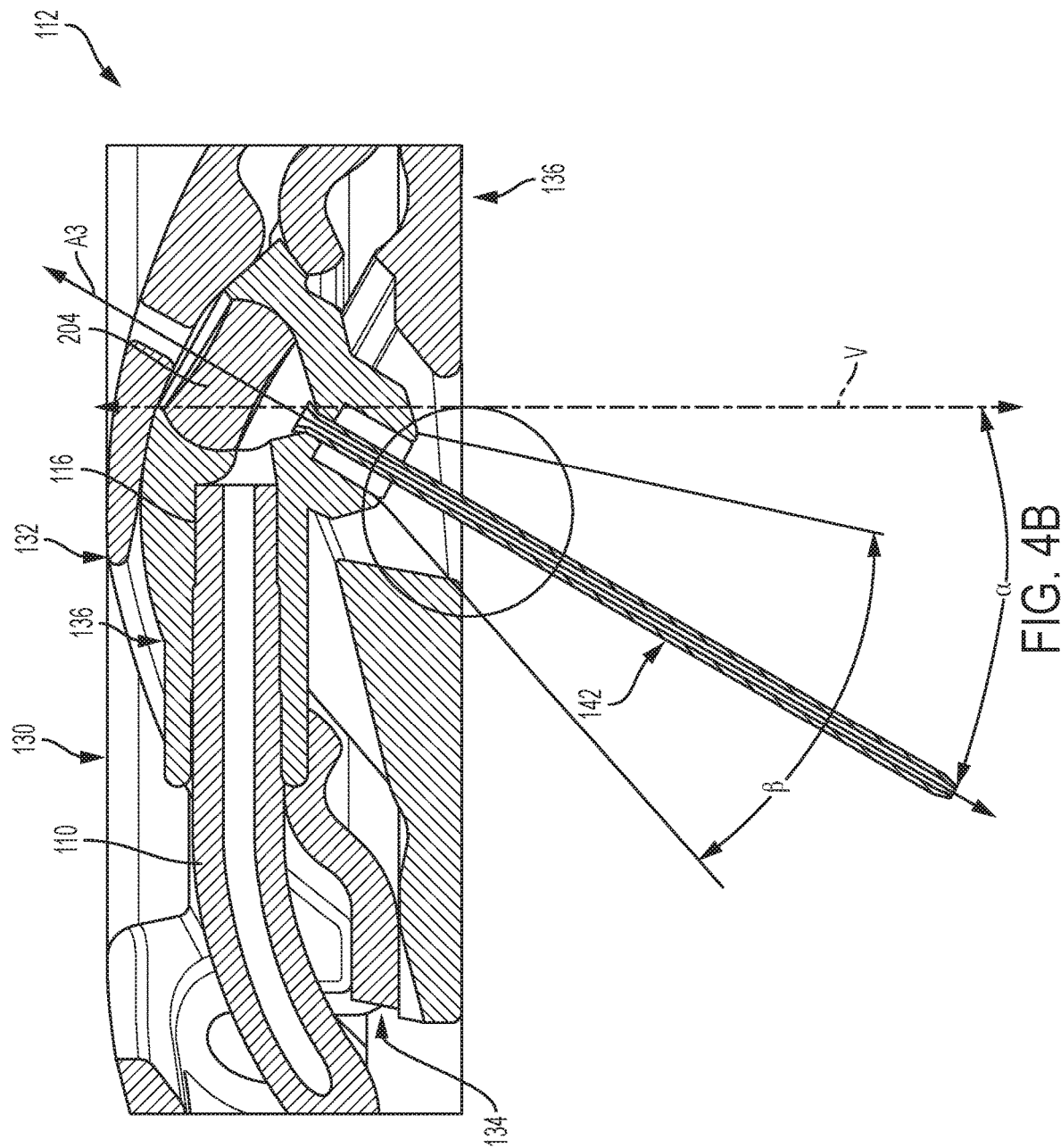

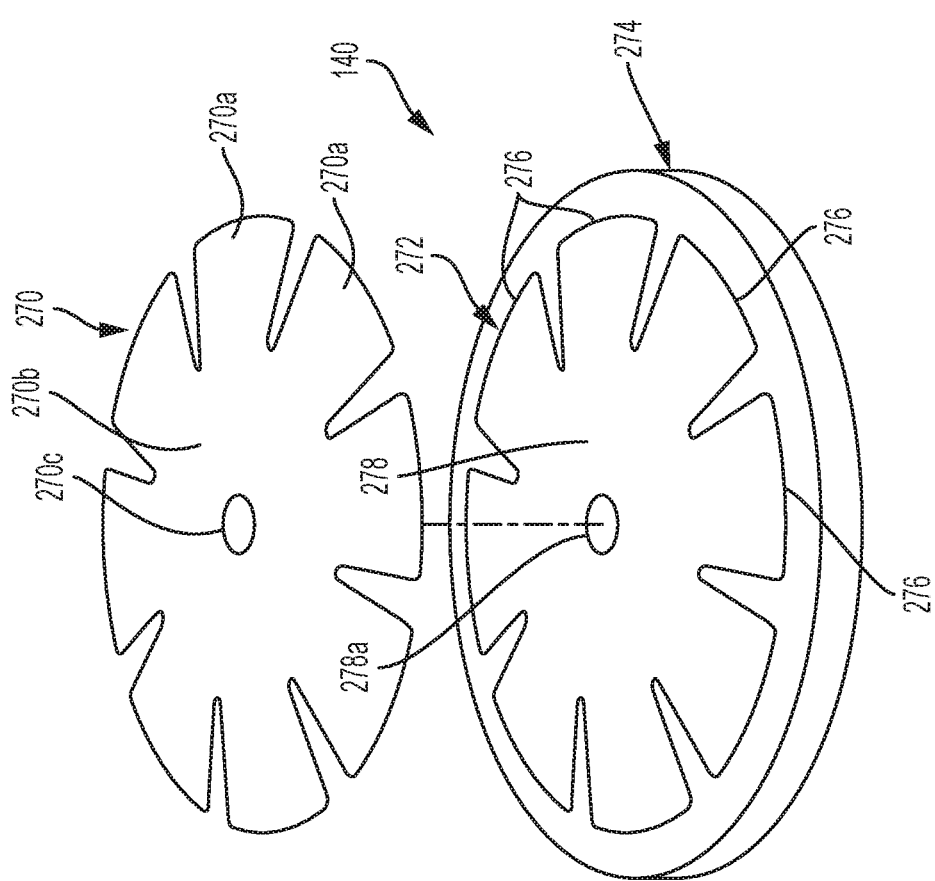

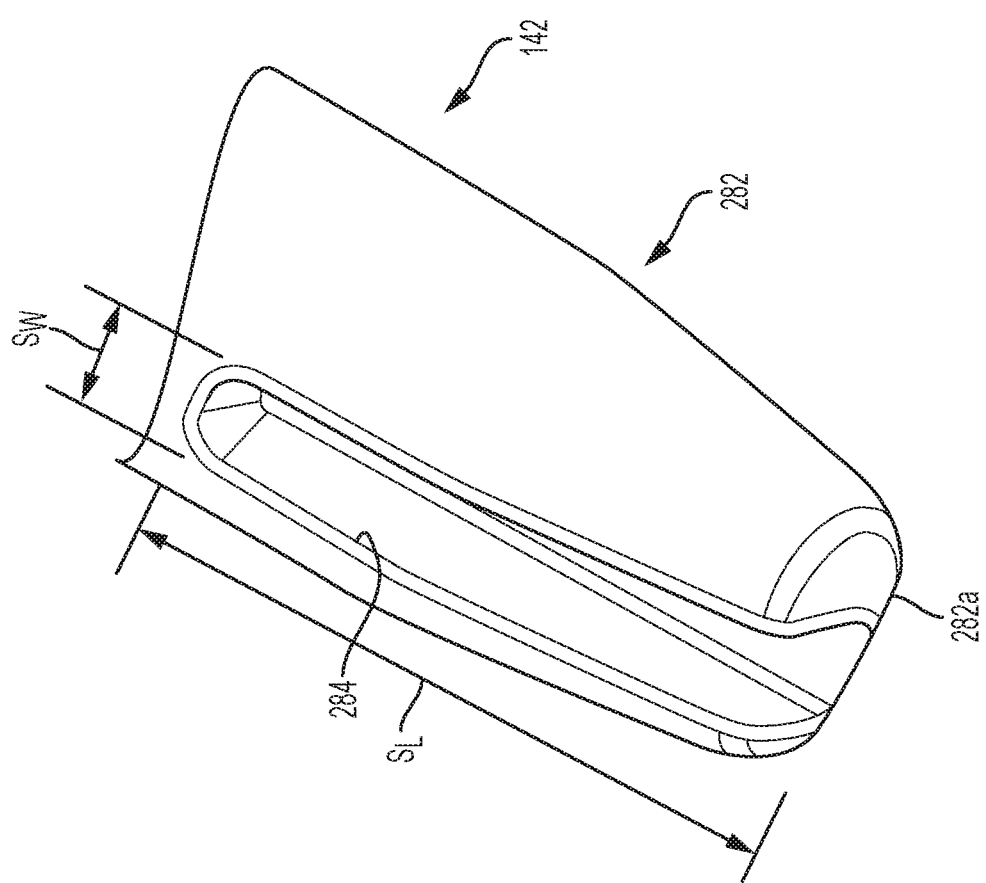

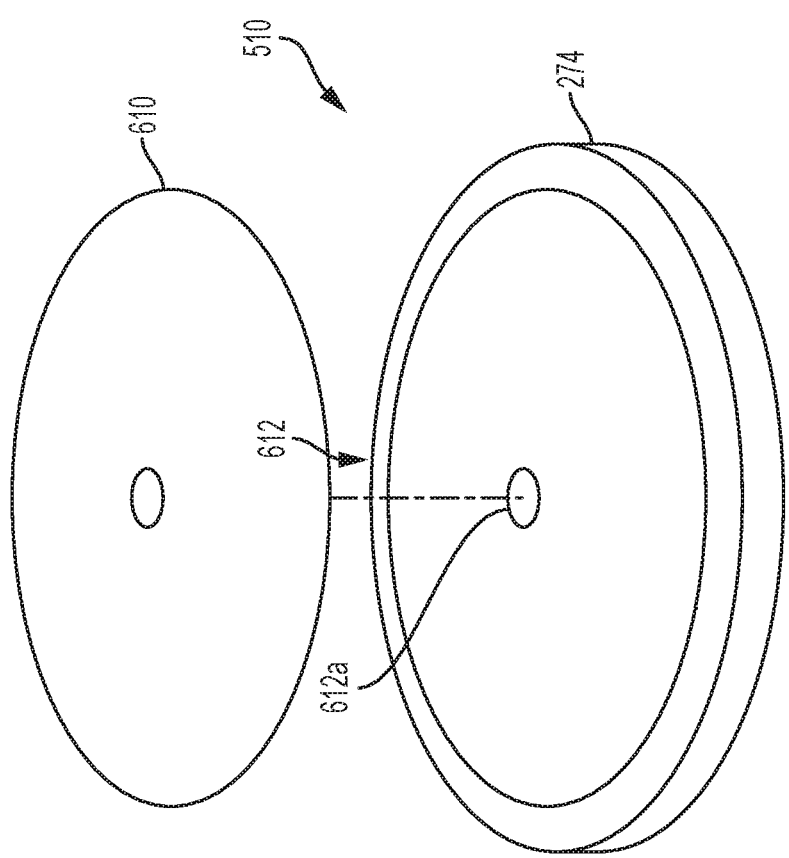

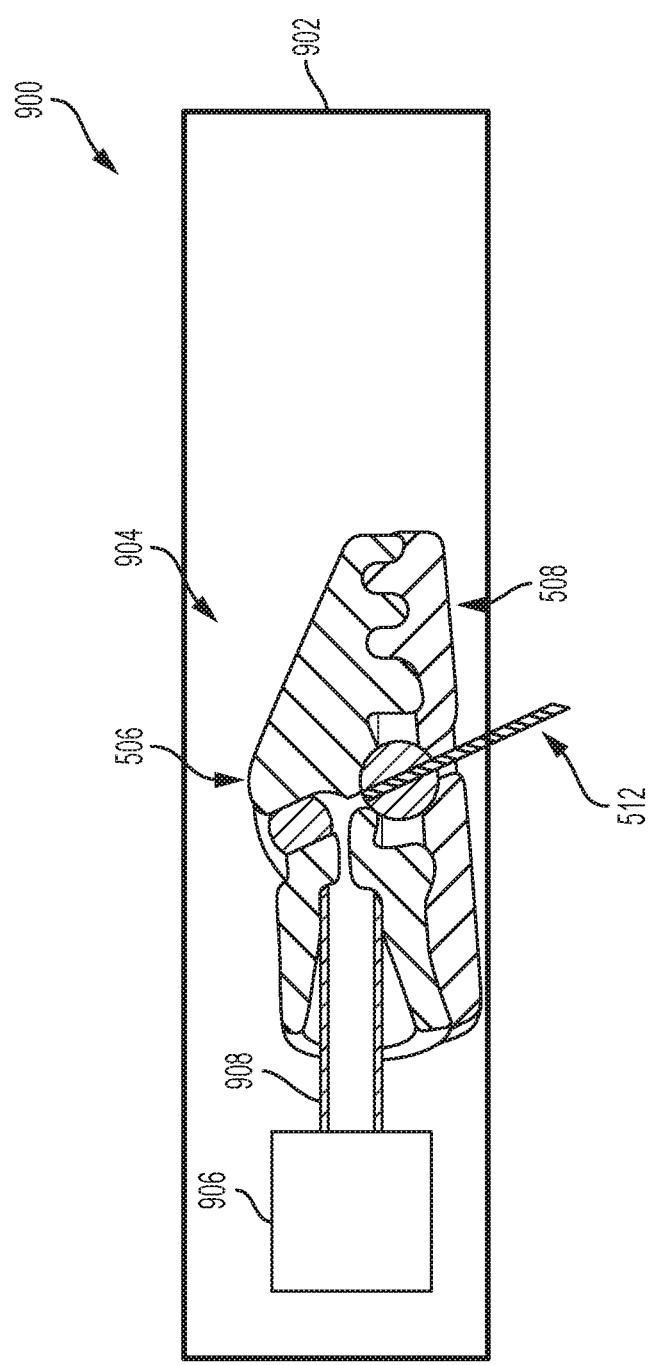

INFUSION SET WITH PIVOTING METAL CANNULA AND STRAIN RELIEF

TECHNICAL FIELD

Embodiments of the subject matter described herein relate generally to medical devices, such as an infusion set for use with a fluid infusion device. More particularly, embodiments of the subject matter relate to an infusion unit of an infusion set for use with a fluid infusion device that has a pivoting metal cannula and integral strain relief.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user. In certain instances, these fluid infusion devices require an insertion set, such as an infusion set, to be coupled to the body of a user for the delivery of the insulin. Generally, the infusion set is coupled to the fluid infusion device via hollow tubing, which provides a fluid flow path from the fluid infusion device to the user. Typically, the infusion set requires a portion of a cannula, for example, to be inserted under the skin of the user to deliver the controlled amounts of insulin from the fluid infusion device to the user via the infusion set.

In certain instances, the cannula inserted under the skin of the user may be composed of a polymer-based material. The polymer-based material, however, is typically not rigid to provide comfort to the user, but the decreased rigidity may result in bending of the cannula during wear by the user. Further, in certain instances, the cannula inserted under the skin of the user may be composed of a rigid material. In these instances, during the wearing of the infusion set by the user, when the hollow tubing is caught on an object, a strain is imparted directly to the infusion set, which may cause the metal cannula to advance into the skin of the user. This may be uncomfortable to the user.

Accordingly, it is desirable to provide an infusion set having a pivoting metal cannula and strain relief for coupling to a user to deliver a fluid from a fluid infusion device to the user. Furthermore, other desirable features and characteristics will become apparent from the subsequent detailed description and the appended claims, taken in conjunction with the accompanying drawings and the foregoing technical field and background.

BRIEF SUMMARY

According to various embodiments, provided is an infusion set for use with a fluid infusion device having a fluid reservoir. The infusion set includes a cannula that provides a fluid flow path and a first housing including an articulation member coupled to the cannula. The articulation member is pivotable relative to the first housing to move the cannula relative to the first housing. The first housing is coupled to a fluid supply line to provide a fluid to the cannula, and the fluid supply line is to be coupled to the fluid reservoir to receive the fluid. The infusion set includes a second housing uncoupled from the first housing that surrounds the first housing and receives a portion of the fluid supply line.

Also provided according to various embodiments is an infusion set for use with a fluid infusion device having a fluid reservoir. The infusion set includes a cannula that provides a fluid flow path and a first housing including an articulation member coupled to the cannula. The articulation member is pivotable relative to the first housing to move the cannula relative to the first housing. The first housing is coupled to a fluid supply line to provide a fluid to the cannula, and the fluid supply line is to be coupled to the fluid reservoir to receive the fluid. The infusion set includes a second housing uncoupled from the first housing that surrounds the first housing. The second housing has a plurality of retaining flanges that cooperate to receive a portion of the fluid supply line such that the portion of the fluid supply line is positioned about a circumference of the second housing.

Further provided according to various embodiments is an infusion set for use with a fluid infusion device having a fluid reservoir. The infusion set includes a metal cannula that provides a fluid flow path and a first housing including an articulation member coupled to the cannula. The articulation member is pivotable relative to the first housing to move the cannula relative to the first housing. The first housing is coupled to a fluid supply line to provide a fluid to the cannula, and the fluid supply line is to be coupled to the fluid reservoir to receive the fluid. The infusion set includes a second housing uncoupled from the first housing that surrounds the first housing. The second housing has a plurality of retaining flanges that cooperate to receive a portion of the fluid supply line such that the portion of the fluid supply line is positioned about a circumference of the second housing. The infusion set includes a coupling device to removably couple the infusion set to an anatomy. The coupling device includes an adhesive layer having a plurality of petals that extend radially outward from a central portion. The first housing and the second housing are each coupled to the coupling device.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 3A is a top perspective view of a mount of the infusion unit of FIG. 2;

FIG. 4B is a detail cross-sectional view of the infusion set of FIG. 2, taken along line 4-4 of FIG. 2, which includes the outer housing of the infusion unit and the hollow tube, but the coupling device is removed for clarity;

FIG. 5 is a partially exploded perspective view of a coupling device of the infusion unit of FIG. 2, in which a mounting layer of the coupling device is partially exploded from a coupling layer and a backing layer of the coupling device;

FIG. 6 is a detail view of a second end of a metal cannula of the infusion unit, taken at 6 on FIG. 3;

FIG. 13 is a partially exploded perspective view of a coupling device of the infusion unit of FIG. 10, in which a mounting layer of the coupling device is partially exploded from a coupling layer and a backing layer of the coupling device;

FIG. 16A is a schematic view of another exemplary embodiment of a fluid infusion device including an infusion unit with a pivotable metal cannula according to various teachings of the present disclosure.

DETAILED DESCRIPTION

Figure 1:
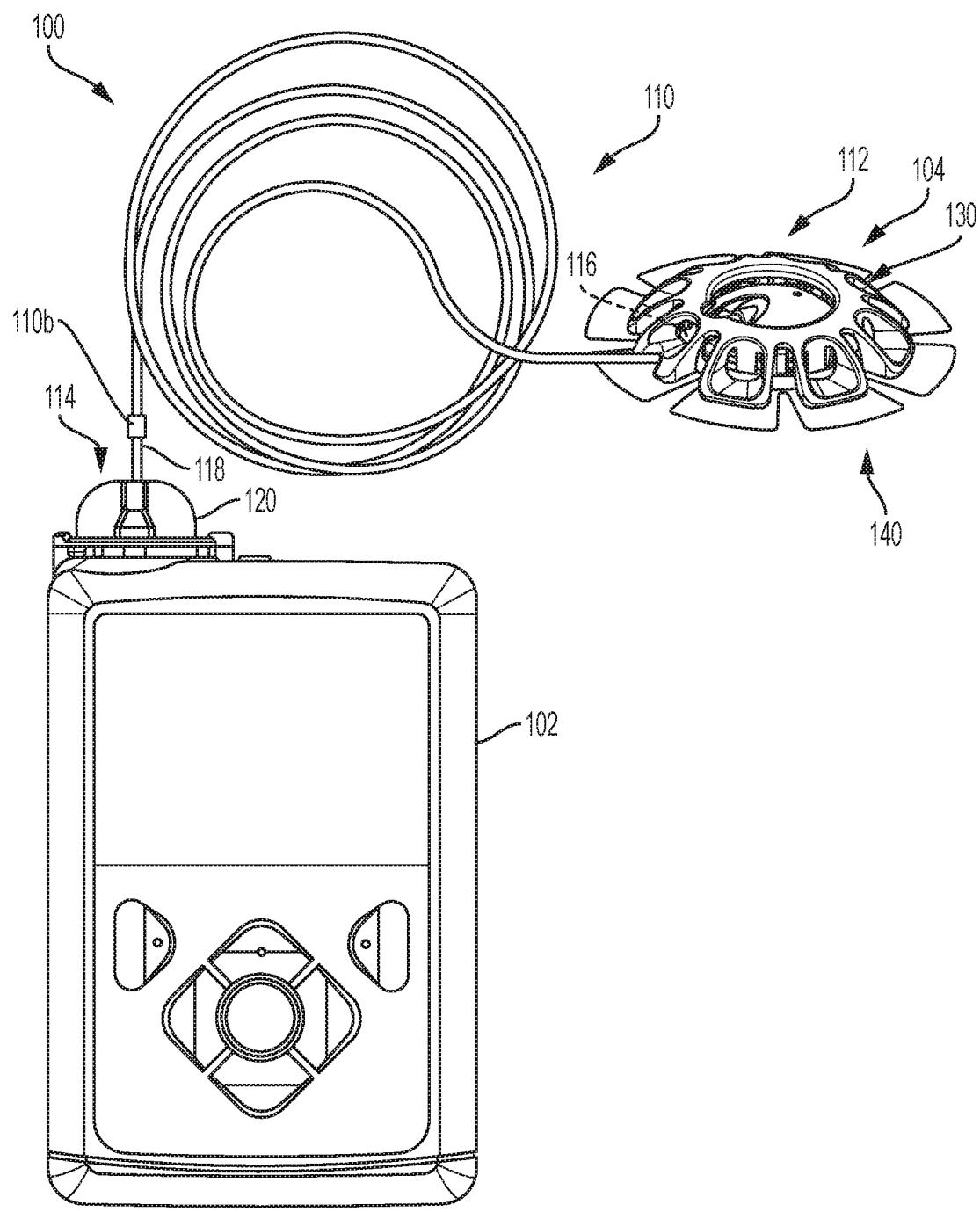
FIG. 1 is a perspective view of an exemplary embodiment of a fluid infusion device including an infusion set having an infusion unit with a pivotable metal cannula and strain relief according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominately in the respective nominal axial or radial direction. As used herein, the term "transverse" denotes an axis that crosses another axis at an angle such that the axis and the other axis are neither substantially perpendicular nor substantially parallel.

The following description generally relates to an infusion set of the type used in treating a medical condition of a user. The infusion set infuses a fluid into a body of the user. The non-limiting examples described below relate to an infusion set used in the treatment of diabetes, although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

FIG. 1 is a perspective view of an exemplary embodiment of a fluid infusion system 100. The fluid infusion system 100 includes two main components: a fluid infusion device 102 (e.g., an insulin pump) and an infusion set 104, which is coupled to the fluid infusion device 102 as depicted in FIG. 1. In one example, the infusion set 104 includes, without limitation: a hollow fluid supply line or tube 110, an infusion unit 112 and a connector assembly 114. The infusion unit 112 is coupled to a first end 116 of the tube 110 and the connector assembly 114 is coupled to a second end 118 of the tube 110. The fluid infusion device 102 is carried or worn by the user, and the infusion set 104 terminates at the infusion unit 112 to enable the fluid infusion device 102 to deliver fluid to the body of the user via the tube 110. Thus, the infusion unit 112 is coupled to the body of the user, as described in more detail below. The fluid infusion device 102 may leverage a number of conventional features, components, elements, and characteristics of existing fluid infusion devices. For example, the fluid infusion device 102 may incorporate some of the features, components, elements, and/or characteristics described in U.S. Pat. Nos. 6,485,465 and 7,621,893, the relevant content of which is incorporated by reference herein. It should be noted that the fluid infusion device 102 illustrated herein is merely exemplary, as any suitable fluid infusion device can be employed with the infusion set 104.

The fluid infusion device 102 accommodates a fluid reservoir (hidden from view in FIG. 1) for the fluid to be delivered to the user. The tube 110 represents the fluid flow path that couples the fluid reservoir to the infusion unit 112. When installed as depicted in FIG. 1, the tube 110 extends from the fluid infusion device 102 to the infusion unit 112, which in turn provides a fluid pathway to the body of the user. In certain embodiments, an in-line connector 110b is coupled between ends of the tube 110 to enable the user to quickly disconnect the tube 110 from the fluid infusion device 102. For example, the in-line connector 110b may comprise a quick release in-line connector such as that associated with the Medtronic Paradigm™ Sof-set® Micro QR or Ultimate Infusion Set, commercially available from Medtronic Minimed, Inc. of Northridge, Calif. For the illustrated embodiment, the connector assembly 114 is realized as a removable reservoir cap 120 (or fitting) that is suitably sized and configured to accommodate replacement of fluid reservoirs (which are typically disposable) as needed. In this regard, the reservoir cap 120 is designed to accommodate the fluid path from the fluid reservoir to the tube 110.

Figure 2:
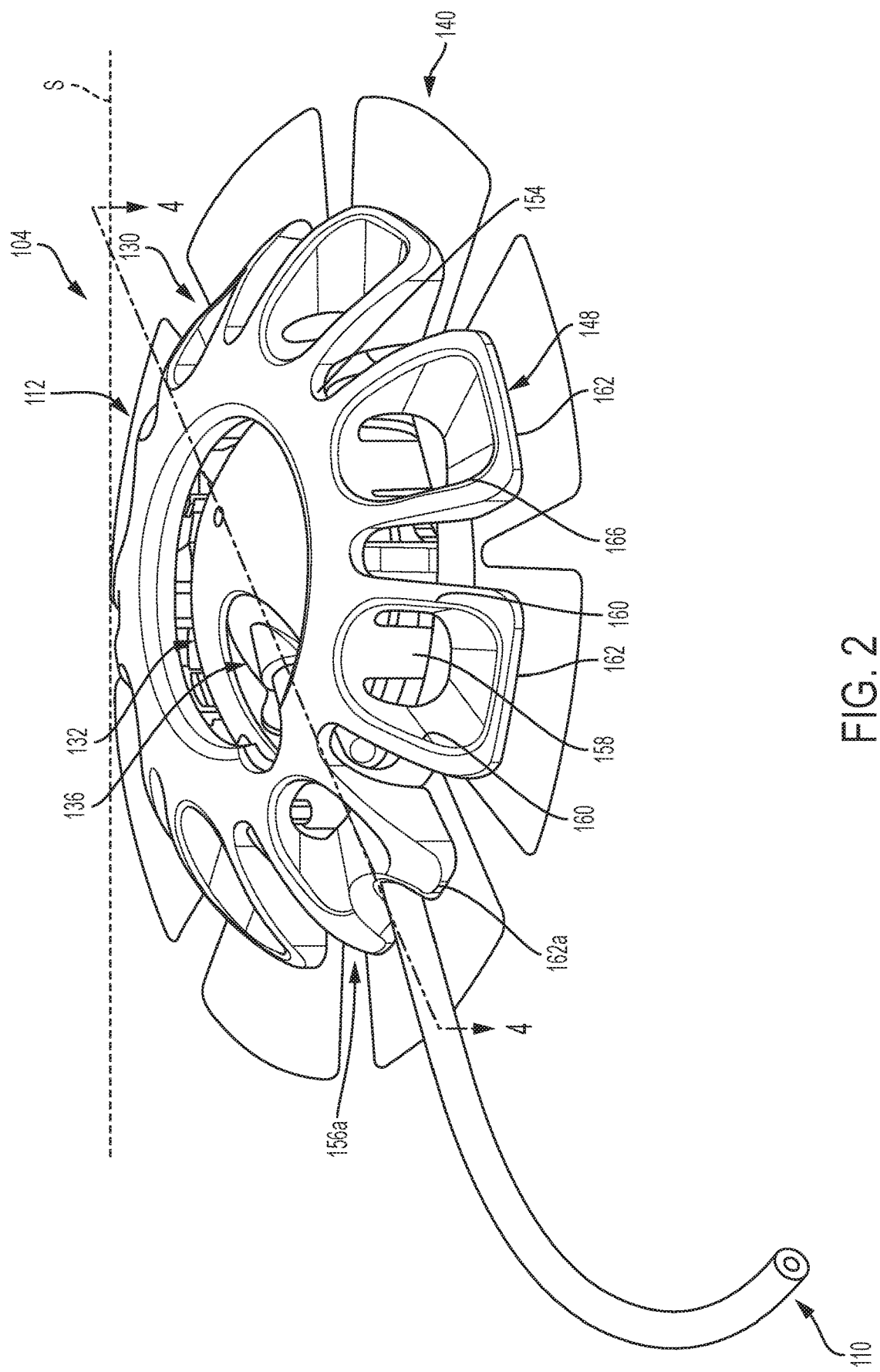
FIG. 2 is an environmental perspective view of an infusion unit and a hollow tube associated with the infusion set of FIG. 1, which illustrates the infusion unit in an installed state.
Figure 3:
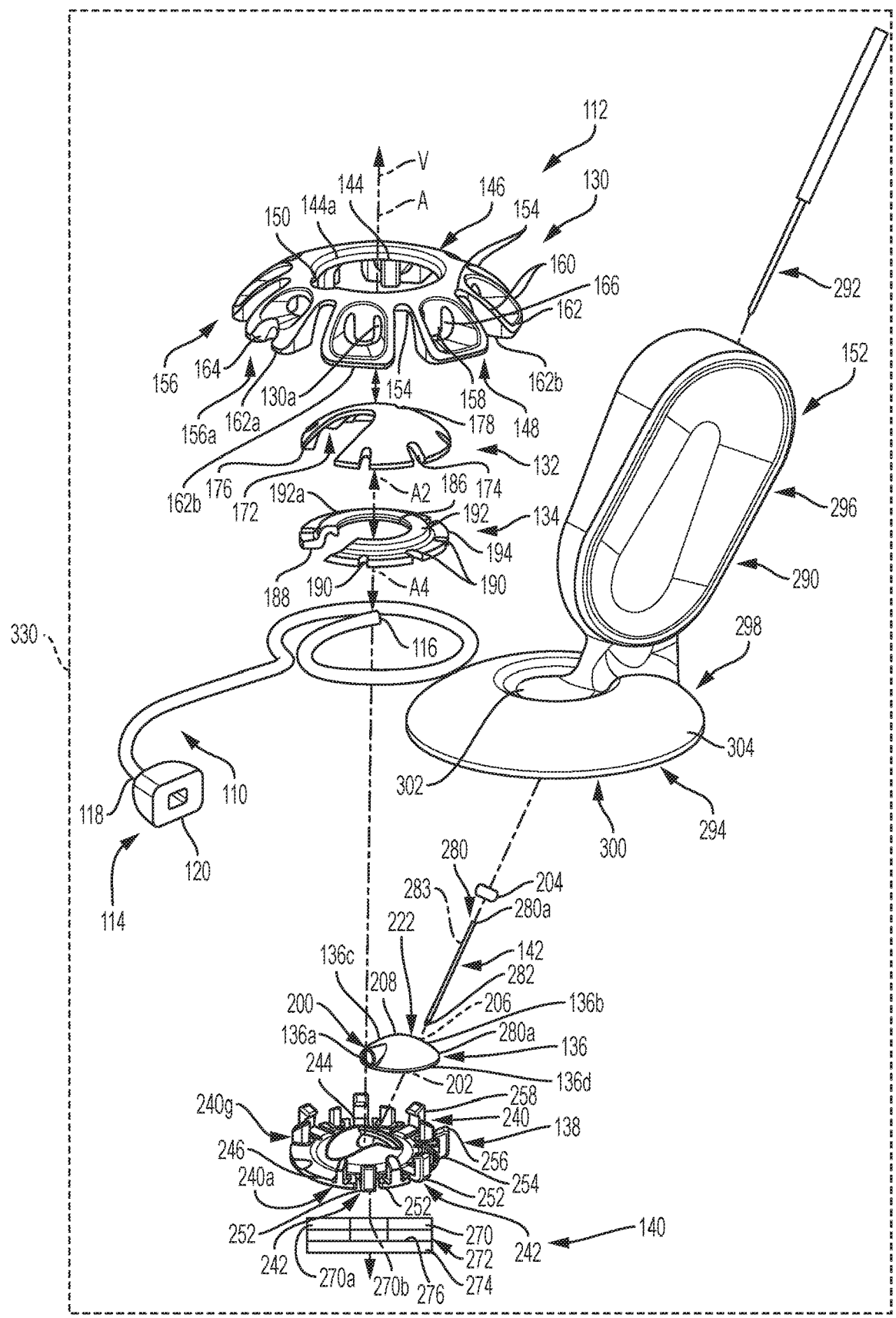
FIG. 3 is an exploded view of a kit for the infusion set of FIG. 1.

With reference to FIG. 2, the infusion unit 112 of the infusion set 104 is shown installed onto a skin S of a user. The infusion unit 112 delivers fluid from the fluid reservoir associated with the fluid infusion device 102 (FIG. 1) received through the tube 110 into the body of the user. In one example, with additional reference to FIG. 3, the infusion unit 112 includes a first or outer housing 130, a second or inner housing 132, a biasing member 134 (FIG. 3), an articulation member or movable needle mount 136, a mount 138 (FIG. 3), a coupling device 140 and a needle or metal cannula 142 (FIG. 3). In this example, as will be discussed, the biasing member 134 (FIG. 3) and the movable needle mount 136 are received within a chamber defined between the inner housing 132 and the mount 138. It should be noted that while the infusion unit 112 is described herein as including the biasing member 134 (FIG. 3), the biasing member 134 may be optional.

The outer housing 130 surrounds the inner housing 132 and the mount 138. Generally, the outer housing 130 circumscribes the inner housing 132 and the mount 138, but is not coupled to the inner housing 132 or the mount 138. The outer housing 130 is uncoupled from or discrete from the inner housing 132 and the mount 138 to provide strain relief to the first end 116 of the tube 110 (FIG. 3). In this regard, by being disjoined from the inner housing 132 and the mount 138, any strain imparted to the tube 110 will be dissipated by the outer housing 130, which reduces a likelihood of the first end 116 of the tube 110 being uncoupled from the movable needle mount 136. In one example, the outer housing 130 is composed of a polymer-based material, including, but not limited to, polypropylene, silicone or a thermoplastic elastomer. The outer housing 130 may be formed through molding, casting, printing, etc. The outer housing 130 is generally concave, however, the outer housing 130 may have any desired shape.

In this example, with reference to FIG. 3, the outer housing 130 includes a central bore 144, an annular hub 146 and a plurality of retaining flanges 148. The central bore 144 is defined through the hub 146 of the outer housing 130 so as to extend along an axis A. The central bore 144 is sized to surround the inner housing 132 and the mount 138. In one example, the central bore 144 includes a notch 150. The notch 150 is defined through a perimeter or circumference 144a of the central bore 144 and is defined so as to extend radially outward from the axis A. The notch 150 provides clearance for the tube 110 as it exits the movable needle mount 136.

Figure 2A:
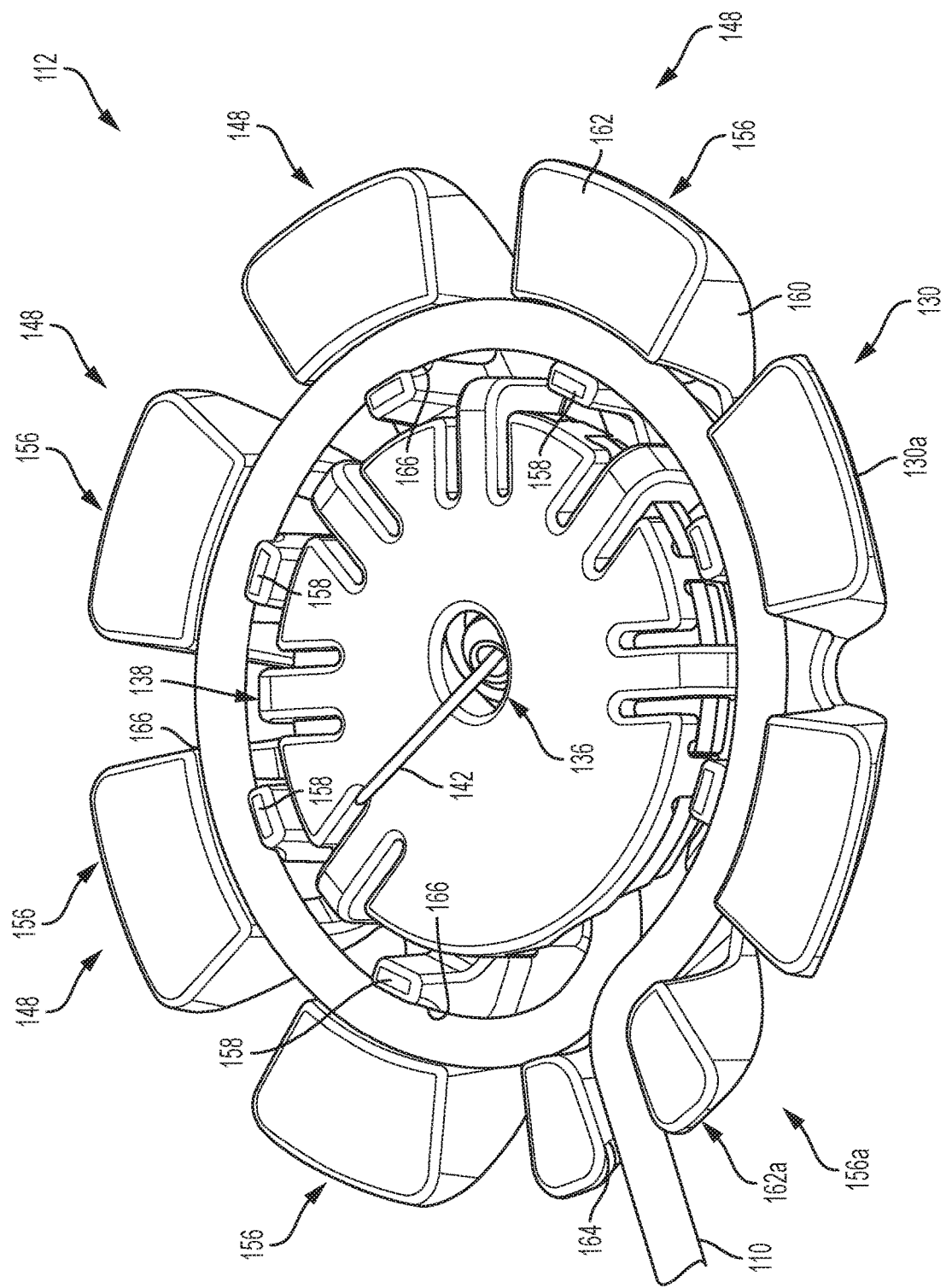
FIG. 2A is a bottom perspective view of the infusion unit and the hollow tube associated with the infusion set of FIG. 1, in which a coupling device is removed for clarity.

The hub 146 may be coupled to the needle hub 152 to install the infusion unit 112 on the user. In one example, the hub 146 surrounds the central bore 144 and is interconnected to each of the plurality of retaining flanges 148. The plurality of retaining flanges 148 are spaced apart about a perimeter or circumference of the hub 146. In one example, each of the plurality of retaining flanges 148 is separated by a respective one of a plurality of slots 154 defined from an outer periphery or perimeter 130a of the outer housing 130 to the hub 146. In one example, the outer housing 130 includes 8 retaining flanges 148, however, the outer housing 130 may include any number of retaining flanges, such as 4 to 16. Each of the retaining flanges 148 includes a flange 156 and a tab 158. The flange 156 includes a pair of sidewalls 160 and a base 162. The pair of sidewalls 160 are coupled to the hub 146 and extend outwardly from the hub 146 at an angle toward the outer perimeter 130a of the outer housing 130. The pair of sidewalls 160 interconnect the hub 146 and the base 162. The base 162 is substantially planar or flat, and is coupled to the coupling device 140. Each of the flanges 156 is substantially the same, except for the flange 156a. A base 162a of the flange 156a has an increased thickness, which enables a cutout 164 to be defined through the base 162a. The cutout 164 enables a portion of the tube 110 to pass through the flange 156a (FIG. 2A). The tab 158 extends axially from the hub 146. The tab 158 cooperates with the flange 156 to retain the tube 110 when the tube 110 is coupled to the movable needle mount 136. In this regard, due to the angle of the pair of sidewalls 160, a retaining recess 166 is defined between the base 162 and the tab 158. With reference to FIG. 2A, the retaining recess 166 receives a portion of the tube 110 to secure the tube 110 to the outer housing 130. Generally, the plurality of retaining flanges 148 cooperate to enable the tube 110 to be positioned about a circumference of the outer housing 130 near the outer perimeter 130a of the outer housing 130.

With reference back to FIG. 3, the inner housing 132 retains the biasing member 134 and the movable needle mount 136 on the mount 138. In one example, the inner housing 132 is composed of a polymer-based material, including, but not limited to, polypropylene, silicone or a thermoplastic elastomer. The inner housing 132 may be formed through molding, casting, printing, etc. The inner housing 132 is generally concave, however, the inner housing 132 may have any desired shape. The inner housing 132 includes an outer surface 170, an inner surface 172, a plurality of coupling slots 174, a clearance aperture 176 and a needle bore 178.

Figure 4:
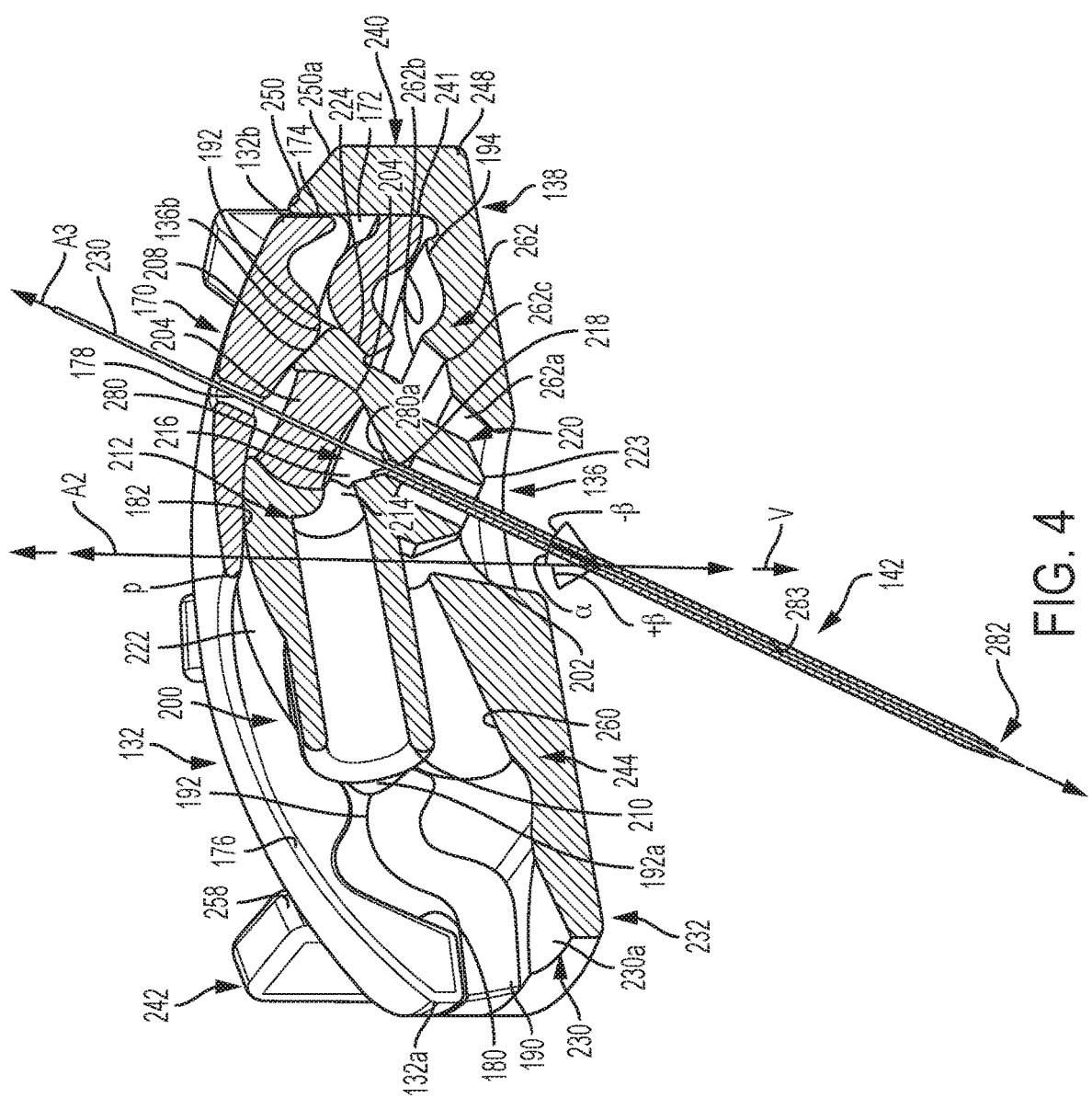
FIG. 4 is a cross-sectional view of the infusion set of FIG. 2, taken along line 4-4 of FIG. 2, in which an outer housing of the infusion unit, the hollow tube and the coupling device are removed for clarity.
Figure 4A:
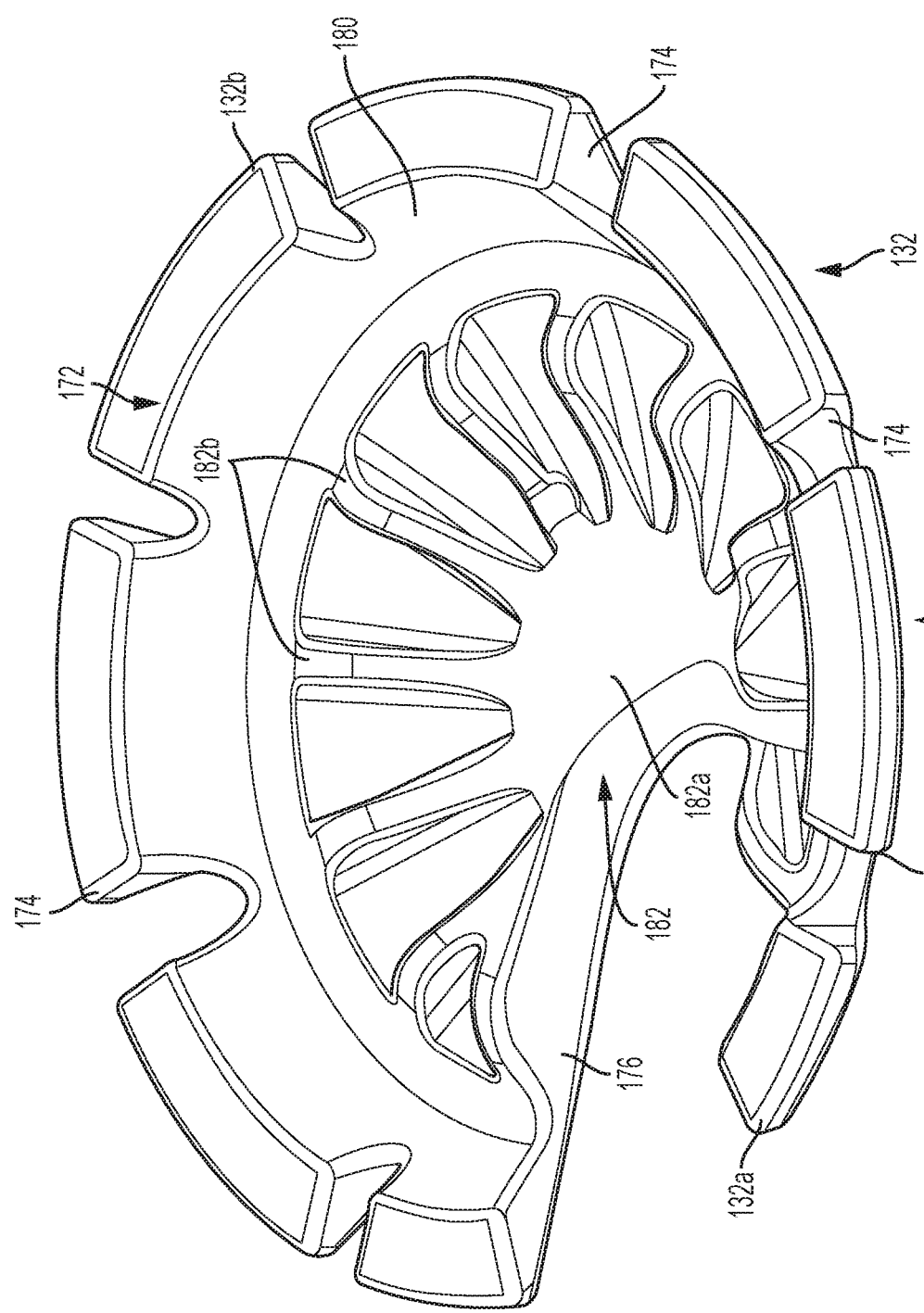
FIG. 4A is a bottom view of an inner housing of the infusion unit of FIG. 2.

The outer surface 170 is substantially smooth, and is substantially conical. The inner surface 172 is opposite the outer surface 170. With reference to FIG. 4, the inner surface 172 includes a biasing member clearance surface 180 and a first articulation surface 182. With reference to FIG. 4A, the biasing member clearance surface 180 extends about a circumference of the inner housing 132 on the inner surface 172. The biasing member clearance surface 180 provides space or room for the biasing member 134 to move between a compressed and a relaxed state during the use of the infusion unit 112. Generally, the biasing member clearance surface 180 has a shape that corresponds to the shape of the biasing member 134 (FIG. 4); however, the biasing member 134 may have any desired shape.

Figure 4C:
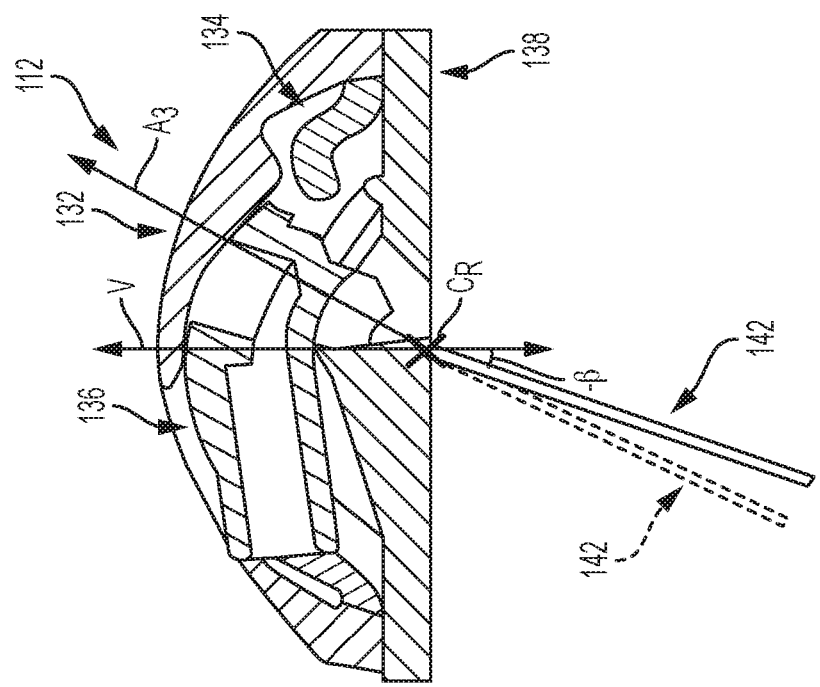
FIG. 4C is a schematic cross-sectional view of the infusion set of FIG. 2, taken along line 4-4 of FIG. 2, in which the outer housing of the infusion unit, the hollow tube and the coupling device are removed for clarity, and a cannula of the infusion unit is pivoted about a positive angle.
Figure 4D:
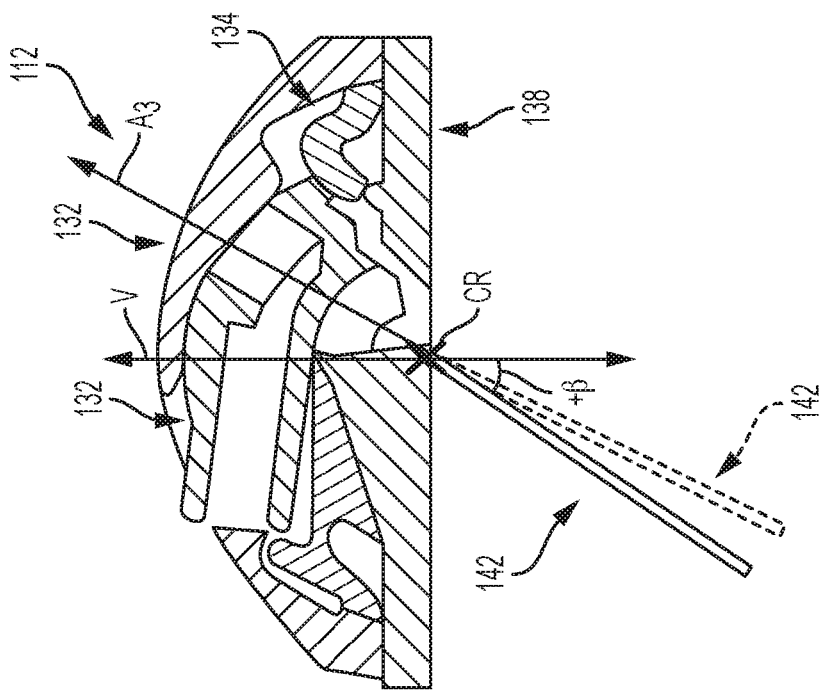
FIG. 4D is a schematic cross-sectional view of the infusion set of FIG. 2, taken along line 4-4 of FIG. 2, in which the outer housing of the infusion unit, the hollow tube and the coupling device are removed for clarity, and a cannula of the infusion unit is pivoted about a negative angle.

The first articulation surface 182 is spherical and concave. The first articulation surface 182 is defined on the inner surface 172 so as to be offset from a central axis A2 of the inner housing 132. The central axis A2 is parallel to the vertical axis V (FIG. 3). In this example, the first articulation surface 182 is offset from the central axis A2 toward a second end 132b of the inner housing 132. Generally, the first articulation surface 182 extends from a first side 172a of the inner surface 172 to a second, opposite side 172b of the inner surface 172 near or adjacent to the second end 132b of the inner housing 132. The first articulation surface 182 may include a central portion 182a with one or more ribs 182b spaced apart and extending radially outward from the central portion 182a. In this example, the one or more ribs 182b cooperate with the central portion 182a to define the first articulation surface 182; however, the first articulation surface 182 may be substantially uniform or continuous. With reference back to FIG. 4, the first articulation surface 182 cooperates with the movable needle mount 136 to enable the cannula 142 to move or pivot relative to an angle α defined between a central vertical axis V of the infusion unit 112 and an axis A3 through a center line of the cannula 142. In one example, with reference to FIG. 4B, the angle α is about 10 degrees to about 45 degrees. In one example, the movable needle mount 136 is movable or pivotable an angle β relative to the angle α. In this example, angle β is about ±5 degrees to about ±20 degrees relative to the angle α. Generally, the center of rotation CR of angle β is approximately at the entry point of the cannula 142 into the skin S (FIG. 2) within about ±2.5 millimeters (mm). It should be noted that the movement of the cannula 142 is conical, and the movement of the cannula 142 about the angle β is a conical movement in and out of the plane shown in FIGS. 4C and 4D. As shown in FIG. 4C, a deflection of the movable needle mount 136 has caused the cannula 142 to rotate a positive angle β relative to the vertical axis V. In FIG. 4D, a deflection of the movable needle mount 136 has caused the cannula 142 to rotate a negative angle β relative to the vertical axis V.

With reference to FIG. 3, the plurality of coupling slots 174 are spaced apart about the perimeter or outer circumference of the inner housing 132. In one example, the inner housing 132 includes about 7 coupling slots 174, which cooperate with the mount 138 to secure the inner housing 132 to the mount 138. In this example, each of the coupling slots 174 is sized to receive a portion of the mount 138 to retain the inner housing 132 on the mount 138. With reference back to FIG. 4, the clearance aperture 176 is defined through the outer surface 170 and the inner surface 172 at a first end 132a of the inner housing 132. In one example, the clearance aperture 176 extends from the perimeter or outer circumference of the inner housing 132 to a point P proximate the central axis A2 of the inner housing 132. The clearance aperture 176 provides space or a volume for the movable needle mount 136 and/or tube 110 to move relative to the inner housing 132. The needle bore 178 is defined through the outer surface 170 and the inner surface 172. The needle bore 178 is generally defined through the inner housing 132 so as to extend through a portion of the first articulation surface 182. Thus, in this example, the needle bore 178 is offset from the central axis A2 of the inner housing 132, and is near the second end 132b of the inner housing 132. In one example, the needle bore 178 extends along an axis that is transverse or oblique to the central axis A2 of the inner housing 132. The needle bore 178 receives a portion of the needle hub 152 (FIG. 3) to install the infusion unit 112 on the user.

Figure 4E:
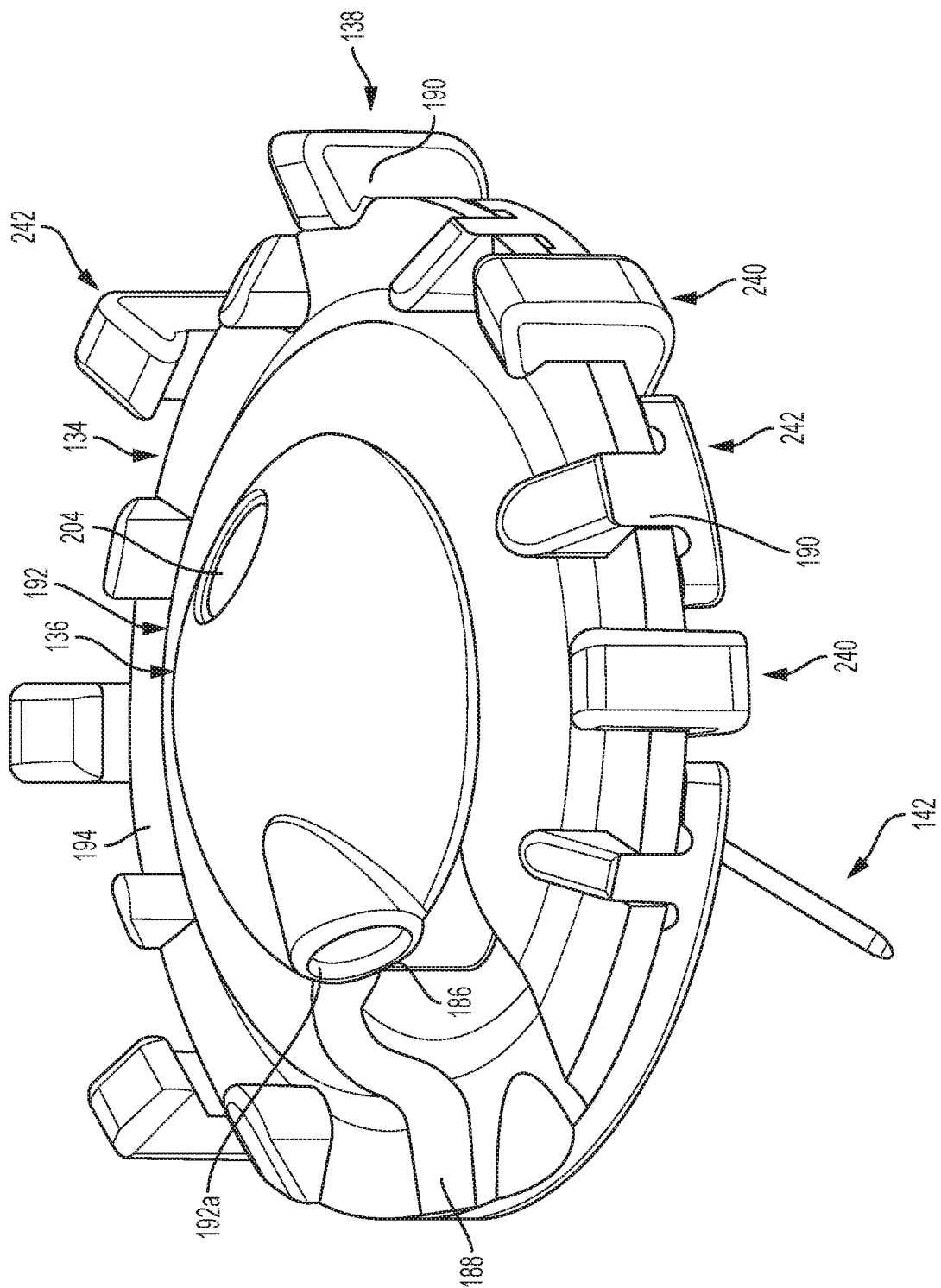
FIG. 4E is a top perspective view of the infusion unit of FIG. 1, in which the outer housing, the inner housing, the hollow tube and the coupling device are removed for clarity.

With reference to FIG. 3, the biasing member 134 returns the movable needle mount 136 to a first, initial or neutral position (FIG. 4). In the neutral position, the movable needle mount 136 is at the angle α relative to the vertical axis V. A movement or pivoting of the movable needle mount 136 compresses the biasing member 134 to provide a spring force to return the movable needle mount 136 to the neutral position. In this example, with reference to FIG. 3, the biasing member 134 is a disc spring, which is substantially annular. The biasing member 134 is composed of an elastomeric material, including, but not limited to, a silicone or thermoplastic elastomer (TPE). The biasing member 134 is molded; however, the biasing member 134 may be formed through any suitable technique. The biasing member 134 includes a central member bore 186, a member clearance bore 188 and a plurality of member slots 190. In one example, the biasing member 134 includes a member hub 192 integrally formed with a member flange 194. In this example, a portion of the perimeter or outer circumference of the inner housing 132 contacts the member flange 194 when the inner housing 132 is coupled to the mount 138, and the movable needle mount 136 contacts a portion of the member hub 192, as shown in FIG. 4E. The member hub 192 is substantially convex, and in one example, the member hub 192 includes a relief 192a that extends about an inner perimeter of the member hub 192. In this example, a portion of the movable needle mount 136 is received within the relief 192a. With reference back to FIG. 3, the central member bore 186 is defined through the member hub 192 and extends along an axis A4, which is substantially parallel to the vertical axis V. The central member bore 186 is sized to receive and cooperate with the movable needle mount 136.

The member clearance bore 188 is defined through the member hub 192 and the member flange 194. The member clearance bore 188 provides room or space for the tube 110 to be received within the movable needle mount 136, and for the movable needle mount 136 and/or the tube 110 to move or pivot. The member clearance bore 188 is defined so as to be aligned with the clearance bore of the inner housing 132. The plurality of member slots 190 are defined through the member flange 194 substantially about the perimeter or outer circumference of the biasing member 134. Generally, the biasing member 134 includes about 7 member slots 190, which are each aligned with a respective one of the coupling slots 174 to enable the inner housing 132 to be coupled to the mount 138 (FIG. 4E). In this example, each of the member slots 190 is sized to enable a portion of the mount 138 pass therethrough (FIG. 4E).

The movable needle mount 136 enables the cannula 142 to move or pivot relative to the inner housing 132, and thus, the infusion unit 112. In one example, the movable needle mount 136 enables the cannula 142 to move or pivot when the skin S (FIG. 2) of the user moves or when an external force or load is applied to the infusion unit 112. In one example, the movable needle mount 136 is composed of a polymer-based material, including, but not limited to, polypropylene, silicone or a thermoplastic elastomer. The movable needle mount 136 may be formed through molding, casting, printing, etc. With reference to FIG. 4, the movable needle mount 136 includes a tube receiving portion 200, a needle guide 202, a septum 204, a septum bore 206 and a second articulation surface 208. In one example, the movable needle mount 136 is substantially conical, but the movable needle mount 136 may have any desired shape.

The tube receiving portion 200 is substantially cylindrical, and is sized to receive the first end 116 of the tube 110 and to cooperate with the tube 110 to define the fluid flow path to the user. The tube receiving portion 200 is defined at a first end 136a of the movable needle mount 136. The tube receiving portion 200 includes a first end 210 and an opposite second end 212. The first end 210 receives a portion of the tube 110 adjacent to the first end 116. The second end 212 is fixedly coupled to the first end 116 of the tube 110, and includes an outlet 214. Generally, the first end 116 of the tube 110 is fixedly coupled to the second end 212 via any suitable technique, including, but not limited to, adhesives, ultrasonic welding, etc. The outlet 214 defines a fluid flow path from the first end 116 of the tube 110 to the cannula 142. The outlet 214 is in fluid communication with the needle guide 202 to direct the fluid from the fluid reservoir of the fluid infusion device 102 into the body of the user.

The needle guide 202 includes an inlet 216, a needle coupling bore 218 and an annular guide 220. The inlet 216 is in fluid communication with the outlet 214 to receive the fluid. In one example, the inlet 216 is funnel shaped to direct the fluid from the outlet 214 into the cannula 142. The needle coupling bore 218 is defined between the inlet 216 and the annular guide 220. The cannula 142 is fixedly coupled to the needle coupling bore 218. In one example, the cannula 142 is fixedly coupled to the needle coupling bore 218 via adhesives, ultrasonic welding, molding, etc. The annular guide 220 extends outwardly about the needle coupling bore 218 toward the mount 138. The annular guide 220 surrounds the cannula 142, and provides a stop for a movement or rotation of the cannula 142. In this regard, the annular guide 220 includes a flat surface 223 that extends about a periphery of the annular guide 220. A portion of the flat surface 223 contacts a portion of the mount 138 to limit a range of motion of the cannula 142.

The septum 204 is coupled to the septum bore 206. In one example, the septum 204 is fixedly coupled to the septum bore 206 via adhesives, ultrasonic welding, press-fit, etc. The septum 204 is generally circular; however, the septum 204 may have any desired shape. The septum 204 serves as a barrier to prevent the ingress and egress of fluids into the fluid flow path defined by the tube 110 and the cannula 142 within the infusion unit 112. The septum 204 is pierceable by an introducer pin 292 of the needle hub 152 to enable the user to install the infusion unit 112. The septum bore 206 is defined through the second articulation surface 208 and is in communication with the inlet 216. The septum bore 206 is sized and shaped to receive the septum 204, and thus, in this example is substantially cylindrical.

The second articulation surface 208 is spherical and convex. The second articulation surface 208 is defined on an outer surface 222 of the movable needle mount 136 so as to be offset from the central axis A2 of the inner housing 132 and the vertical axis V that extends through the infusion unit 112. In this example, the movable needle mount 136 is offset from the vertical axis V toward a second end 136b of the movable needle mount 136. Generally, with reference to FIG. 3, the second articulation surface 208 extends from a first side 136c of the outer surface 222 of the movable needle mount 136 to a second, opposite side 136d of the outer surface 222 of the movable needle mount 136 near or adjacent to the second end 136b of the movable needle mount 136. Generally, the second articulation surface 208 cooperates with the first articulation surface 182 to enable the cannula 142 to move or pivot positive or negative the angle β relative to the angle α. Generally, with reference to FIG. 4D, the first articulation surface 182 and the second articulation surface 208 are defined on the infusion unit 112 such that the center of rotation CR of the cannula 142 is located near the entry point of the cannula 142 into the skin S of the user (FIG. 2). The rotation of the cannula 142 about the vertical axis V of the infusion unit 112 is symmetric and conical, however, it should be understood that the angle of rotation of the cannula 142 may be asymmetrical, if desired.

In this example, with reference to FIG. 4, the movable needle mount 136 also includes a ledge 224. The ledge 224 is defined about a perimeter of the movable needle mount 136, and is sized to be received within the relief 192a of the member hub 192. In this example, the ledge 224 contacts and rests on the relief 192a of the member hub 192 so that the biasing member 134 may apply the spring force to the movable needle mount 136 to return the movable needle mount 136 to the neutral position.

With reference to FIG. 3, the mount 138 is coupled to the coupling device 140 and to the inner housing 132. The mount 138 is substantially circular; however, the mount 138 may have any desired shape. In one example, the mount 138 is composed of a polymer-based material, including, but not limited to, polypropylene, silicone or a thermoplastic elastomer. The mount 138 may be formed through molding, casting, printing, etc. The mount 138 includes a first mount surface 230, a second mount surface 232 opposite the first mount surface 230 and a central mount bore 234. The first mount surface 230 includes a plurality of projections 240, a plurality of snap fingers 242 and a needle mount interface 244.

The plurality of projections 240 extend axially upward from a perimeter or outer circumference of the first mount surface 230 of the mount 138. In one example, the mount 138 includes 7 projections 240; however, the mount 138 may have any number of projections 240. Each of the plurality of projections 240 are spaced apart about the perimeter of the mount 138 from a first projection 240a to a last projection 240g. A clearance 246 is defined between the first projection 240a and the last projection 240g to enable the tube 110 to be received within the infusion unit 112. Stated another way, the projections 240 are spaced about the perimeter of the mount 138 between the first projection 240a and the last projection 240g to define the clearance 246. With reference to FIG. 4, each of the projections 240 includes a first end 248 and an opposite second end 250. The first end 248 is integrally formed with the mount 138, and the second end 250 is a free end. The second end 250 may include a curvature or taper 250a that corresponds with the outer surface 170 of the inner housing 132 to provide an aesthetically pleasing appearance. An inner surface 241 of each of the projections 240 contacts the biasing member 134 and the inner housing 132 to assist in retaining the biasing member 134 and the inner housing 132 on the mount 138.

With reference to FIG. 3A, the plurality of snap fingers 242 are defined so as to be cantilevered relative to the mount 138 to enable the snap fingers 242 to move or flex to couple the inner housing 132 to the mount 138. In one example, a slot 252 is defined on respective sides of each of the snap fingers 242 to enable the respective snap finger 242 to move relative to the mount 138. Each of the snap fingers 242 extend axially upward from the perimeter or outer circumference of the first mount surface 230 of the mount 138. Each of the snap fingers 242 includes a first end 254 and an opposite second end 256. The first end 254 is integrally formed with the mount 138, and the second end 256 includes a hook 258. With reference to FIG. 4, the hook 258 cooperates with the outer surface 170 of the inner housing 132 to couple the inner housing 132, the biasing member 134 and the movable needle mount 136 to the mount 138. Thus, generally, the inner housing 132, the biasing member 134 and the movable needle mount 136 are snap fit to the mount 138. In this example, the mount 138 includes about 6 snap fingers 242; however, the mount 138 may include any number of snap fingers. Furthermore, in certain embodiments, the mount 138 need not include the snap fingers 242, as the mount 138 may be coupled to the inner housing 132 via an adhesive, ultrasonic welding, etc.

The needle mount interface 244 cooperates with the movable needle mount 136 to limit an amount of movement or rotation of the movable needle mount 136. In one example, with reference to FIG. 4, the needle mount interface 244 includes a first ramp surface 260 and a contoured surface 262. The first ramp surface 260 provides a stop or contact surface for the tube receiving portion 200 of the movable needle mount 136, which limits a movement or rotation of the movable needle mount 136. In one example, the first ramp surface 260 has an incline that is shaped to cooperate with an outer surface of the tube receiving portion 200. It should be noted, however, that the first ramp surface 260 may have any desired shape to provide a stop for a movement of the tube receiving portion 200. The contoured surface 262 has a shape that is configured to match an exterior surface of the inlet 216 and the annular guide 220 of the movable needle mount 136. In one example, the contoured surface 262 includes an inclined surface 262a, a flat surface 262b and a rib 262c. Each of the inclined surface 262a, the flat surface 262b and the rib 262c cooperate to limit a further advancement or movement of the cannula 142, for example, when the inner housing 132 is compressed by an external force. In the example of a compression of the inner housing 132 by the external force, an exterior surface of the annular guide 220 contacts the inclined surface 262a and an exterior surface of the inlet 216 contacts the flat surface 262b and the rib 262c.

The first mount surface 230 may also include a concave relief 230a. The concave relief 230a may receive a portion of the tube 110 during a movement or pivoting of the movable needle mount 136. The second mount surface 232 is substantially flat or planar. The second mount surface 232 is coupled to the coupling device 140. With reference to FIG. 4, the central mount bore 234 is defined through the first mount surface 230 and the second mount surface 232. In one example, the central mount bore 234 is defined through the needle mount interface 244 of the first mount surface 230. The cannula 142 and a portion of the annular guide 220 extend through the central mount bore 234.

With reference to FIG. 3, the coupling device 140 removably couples or secures the mount 138 of the infusion unit 112 to the body of the user. In one example, the coupling device 140 includes a mounting layer 270, an adhesive layer 272 and a backing 274. It should be noted that the mounting layer 270 and the adhesive layer 272 are illustrated herein as having a nominal thickness, but that the mounting layer 270 and the adhesive layer 272 could have any suitable thickness as necessary for the manufacture of the coupling device 140. The mounting layer 270 and adhesive layer 272 may be separately or integrally formed. The mounting layer 270 couples or fixedly attaches the adhesive layer 272 to the second mount surface 232 of the mount 138. The mounting layer 270 may be coupled or secured to the second mount surface 232 of the mount 138 through any suitable technique, including, but not limited to, ultrasonic welding. Generally, the mounting layer 270 is coupled to substantially the entirety of the second mount surface 232 of the mount 138 and a surface 162b associated with each base 162 of the retaining flanges 148 of the outer housing 130. Thus, in one example, the mounting layer 270 is fixedly coupled to the mount 138 and to the outer housing 130. It should be noted, however, that while the mounting layer 270 is illustrated herein as being defined over substantially an entire surface of the coupling device 140, the mounting layer 270 may be coupled to just a portion of the surface of the adhesive layer 272. For example, the mounting layer 270 may be coupled to the adhesive layer 272 so as to extend over a portion of the adhesive layer 272 that corresponds with the portion of the coupling device 140 that is coupled to the mount 138 and/or the outer housing 130. In other words, the mounting layer 270 may be sized to correspond to the size of the mount 138 and/or outer housing 130, and can have a shape that may be different than a shape of the adhesive layer 272.

The adhesive layer 272 enables the infusion unit 112 to be removably coupled to the body of the user. It should be noted that the use of the adhesive layer 272 is merely exemplary, as any suitable technique could be used to removably couple the infusion unit 112 to the user. In one example, with reference to FIG. 5, the adhesive layer 272 is shown in greater detail. In this example, the adhesive layer 272 defines a plurality of projections or petals 276, which extend radially outward from a central portion 278 of the adhesive layer 272. Generally, the adhesive layer 272 includes a petal 276 for each one of the retaining flanges 148 of the outer housing 130. Thus, in this example, the adhesive layer 272 includes 8 petals 276; however, the adhesive layer 272 may include any number of petals.

In the example of the mounting layer 270 being shaped to correspond to the adhesive layer 272, with reference back to FIG. 3, the mounting layer 270 also includes a plurality of petals 270a. Each of the petals 270a of the mounting layer 270 are coupled to the surface 162b of a respective one of the bases 162, while a central portion 270b of the mounting layer 270 is coupled to the mount 138. Similarly, each of the petals 276 of the adhesive layer 272 may be coupled to the skin S (FIG. 2) of the user and the central portion 278 of the adhesive layer 272 may be coupled to the skin S of the user. By providing the mounting layer 270 and the adhesive layer 272 with the petals 270a, 276, less strain is applied to the skin S (FIG. 2) of the user. The central portion 270b of the mounting layer 270 includes a bore 270c, which is sized to enable a portion of the cannula 142 to pass therethrough. With reference back to FIG. 5, the central portion 278 of the adhesive layer 272 also includes a bore 278a, which is also sized to enable a portion of the cannula 142 to pass therethrough. The backing 274 is coupled to at least a portion of the adhesive layer 272, and is removable to facilitate coupling the coupling device 140 to the user, as is generally known. It should be noted that while the mounting layer 270 and the adhesive layer 272 are illustrated and described herein as including the petals 270a, 276, respectively, the mounting layer 270 and/or the adhesive layer 272 need not include the petals 270a, 276. Rather, one or both of the mounting layer 270 and the adhesive layer 272 may be circular, such as that shown in FIG. 13.

With reference back to FIG. 3, the cannula 142 delivers the fluid from the tube 110 into the body of the user. In this example, the cannula 142 is composed of a biocompatible metal or metal alloy, including, but not limited to, titanium, nickel-titanium alloy, titanium alloy, stainless steel, etc. It should be noted that the use of a cannula 142 composed of titanium, nickel-titanium alloy or titanium alloy results in the cannula 142 having increased flexibility when compared to a cannula 142 composed of a stainless steel. Thus, the use of titanium, nickel-titanium alloy or titanium alloy for the cannula 142 may provide the user with improved comfort. In one example, the cannula 142 has an outside diameter that is about or less than 30 gauge, and in one example, the cannula 142 comprises, but is not limited to, a 29 gauge cannula, a 29 gauge thin wall (29TW) cannula, a 29 gauge extra thin wall (29XTW), a 30 gauge, a 30 gauge thin wall (30TW) or a 30 gauge extra thin wall (30XTW). By reducing the thickness of the wall of the cannula 142 through the use of the thin wall or extra thin wall cannulas 142, an outside diameter of the introducer pin 292 may be increased relative to the outside diameter of the cannula 142, which results in less insertion strain when the cannula 142 follows the introducer pin 292 into the skin of the user. The use of the thin wall or extra thin wall cannulas 142 provides for a larger inner diameter for the cannula 142, which may reduce occlusions. The cannula 142 includes a first cannula end 280 and an opposite second cannula end 282. The cannula 142 includes a central needle bore 283, which extends from the first cannula end 280 to the second cannula end 282. The central needle bore 283 enables a portion of the needle hub 152 and the fluid from the tube 110 to pass therethrough.

With reference to FIG. 4, in one example, the first cannula end 280 includes a flared portion 280a. The flared portion 280a is shaped to correspond with the funnel shape of the inlet 216. The flared portion 280a and the funnel shape of the inlet 216 cooperate to direct the introducer pin 292 into the cannula 142. It should be noted that the flared portion 280a of the cannula 142 may be optional, and the cannula 142 may include a cylindrical or un-flared end, if desired.

With reference to FIG. 6, the second cannula end 282 is shown in greater detail. In one example, the second cannula end 282 has a blunt tip 282a and includes a slot 284. By providing the second cannula end 282 with the blunt tip 282a, the cannula 142 does not pierce the internal tissue beneath the skin (FIG. 2) when the infusion unit 112 is compressed against the skin S post insertion, and does not pierce the internal tissue beneath the skin S when the cannula 142 rotates. Thus, the use of the blunt tip 282a may reduce site inflammation and discomfort relative to a cannula with a sharp tip. In one example, the blunt tip 282a has a chamfer to minimize discomfort when the cannula 142 follows the introducer pin 292 into the skin of the user during insertion of the cannula 142. The slot 284 extends from the blunt tip 282a for a slot length $S_L$ of the cannula 142. In one example, the slot length $S_L$ is about 0.25 millimeters (mm) to about 2.0 millimeters (mm). The slot 284 has a slot width $S_W$, which is about 0.05 millimeters (mm) to about 0.24 millimeters (mm). The slot 284 may reduce a potential for occlusions at the second cannula end 282 caused by a compressive force applied to the blunt tip 282a. The slot 284 may be formed in the cannula 142 by laser-cutting, however, other machining techniques may be employed. It should be noted that while the second cannula end 282 is shown and described herein as including the slot 284, the cannula 142 need not include the slot 284, if desired.

Figure 7:
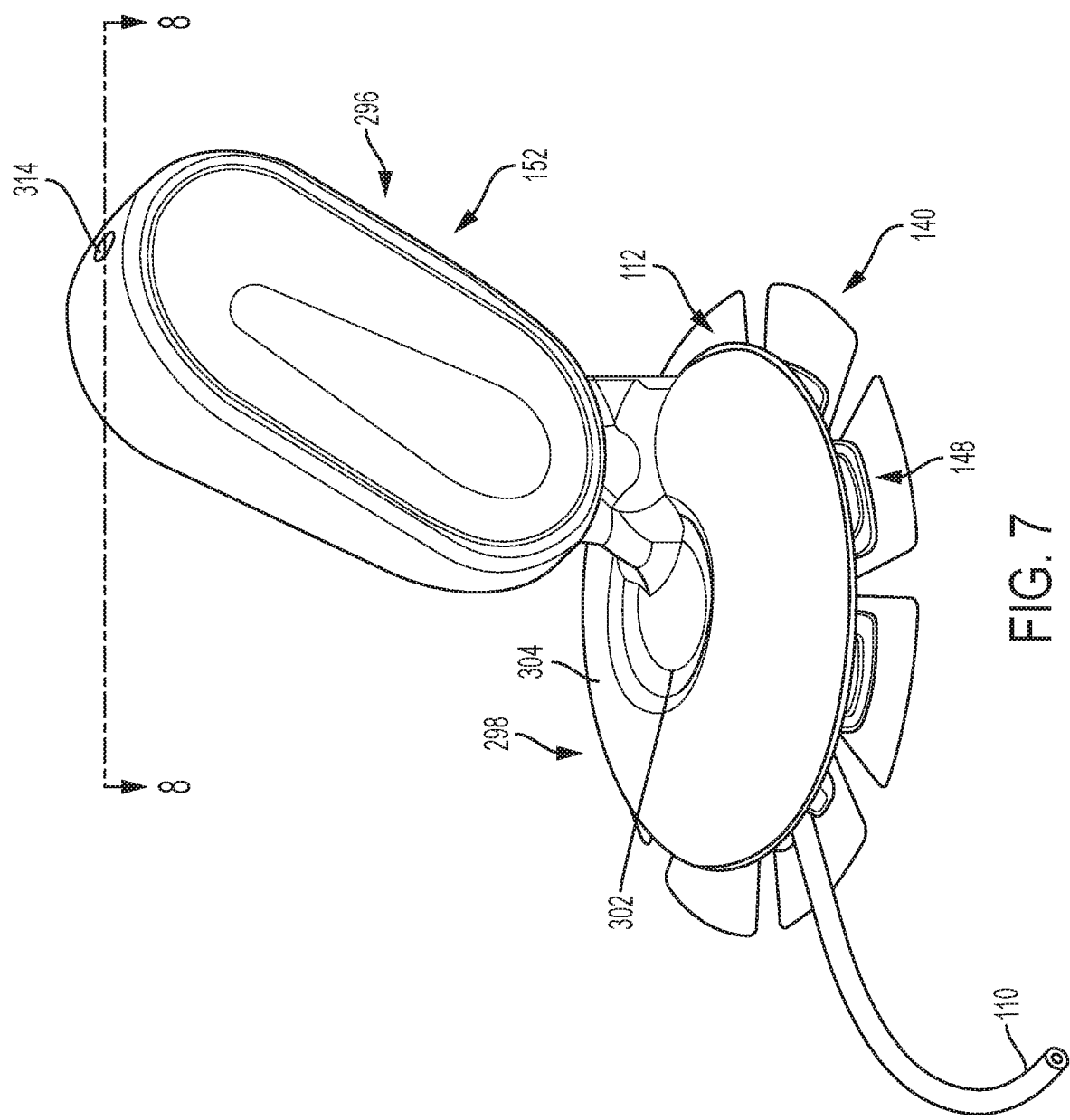
FIG. 7 is a perspective view of a needle hub for use with the infusion set of FIG. 1, in which the needle hub is coupled to the infusion set.

With reference back to FIG. 3, the needle hub 152 is used by a user to install the cannula 142 into to the body of the user. In one example, the needle hub 152 includes a hub body 290 and a removable introducer pin 292. The hub body 290 is composed of a polymer-based material, including, but not limited to polypropylene, polycarbonate, polyester, acrylonitrile butadiene styrene (ABS), acetal and blends of these polymer-based materials. In this example, with reference to FIG. 7, the hub body 290 includes a hub base 294 and a graspable portion or handle 296. It should be noted that although not shown herein, the handle 296 may be modified to integrate with an insertion aid device, including, but not limited to, a MiniMed Sil-serter®, MiniMed Quick-serter® each commercially available from Medtronic Minimed, Inc. of Northridge, Calif. or the like, to assist the user in inserting the cannula 142 at an angle into the skin. The hub base 294 has a first hub side 298 and a second hub side 300. The first hub side 298 includes a recessed midsection 302 and a convex flange 304. It should be noted, however, that the first hub side 298 may have any desired shape. The recessed midsection 302 cooperates with the second hub side 300 to contact a portion of the infusion unit 112 when the needle hub 152 is coupled to the infusion unit 112. The convex flange 304 extends about a perimeter of the recessed midsection 302, and is intersected by the handle 296. The convex flange 304 surrounds a perimeter of the outer housing 130 when coupled to the infusion unit 112 and assists in distributing a force applied by the user to ensure that an entirety of the adhesive layer 272 is coupled to the skin S of the user.

Figure 8:
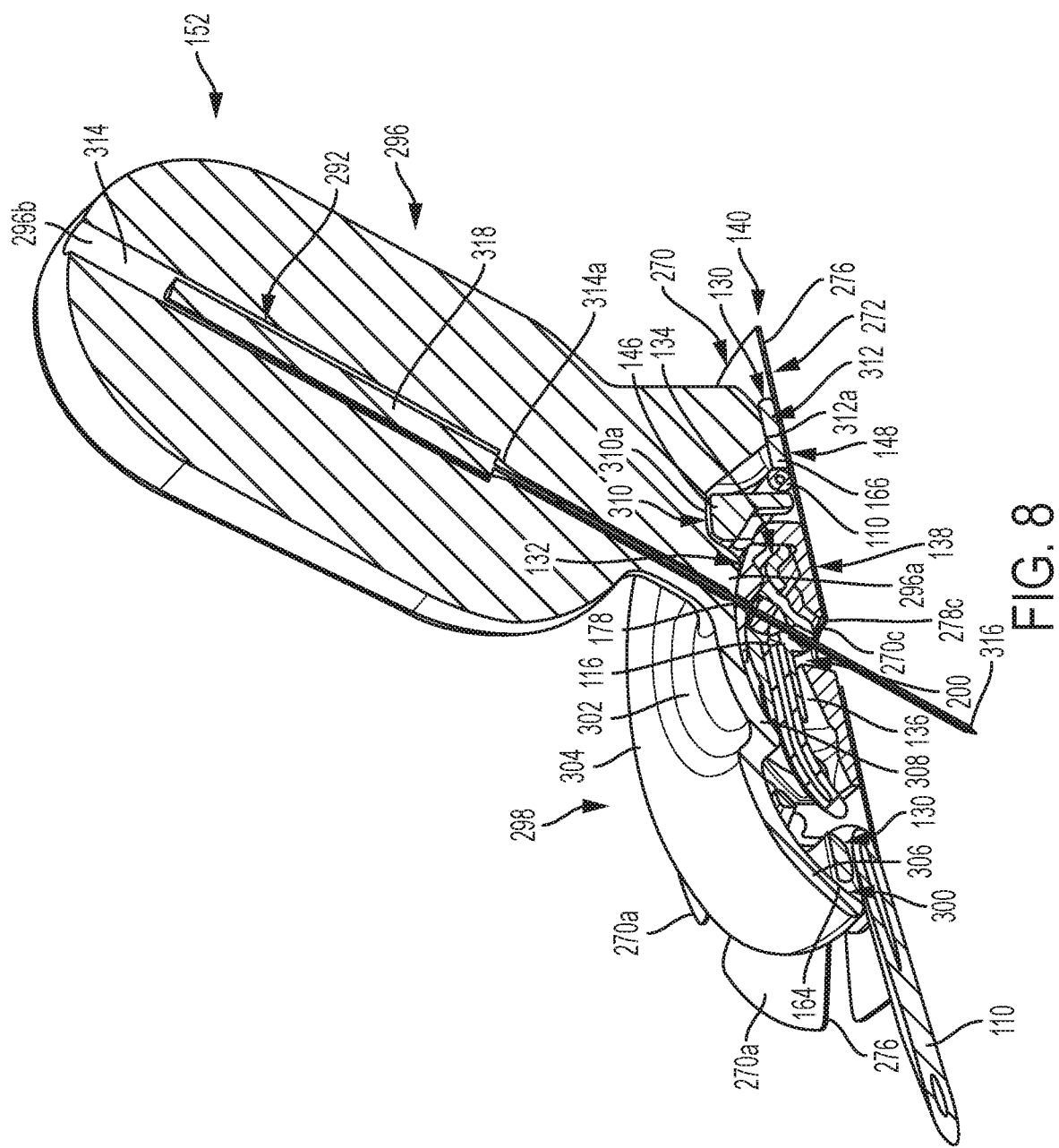
FIG. 8 is a cross-sectional view of the needle hub and the infusion set of FIG. 7, taken along line 8-8 of FIG. 7.

With reference to FIG. 8, the second hub side 300 of the hub base 294 is shown. The second hub side 300 includes a first concave portion 306 and a second concave portion 308. The first concave portion 306 is opposite the convex flange 304. The first concave portion 306 is coupled to and contacts the outer housing 130 when the needle hub 152 is coupled to the infusion unit 112. The second concave portion 308 is opposite the recessed midsection 302. The second concave portion 308 is coupled to and contacts the inner housing 132 when the needle hub 152 is coupled to the infusion unit 112.

The handle 296 is integrally formed with the hub body 290. The handle 296 enables the user to manipulate the needle hub 152 for coupling the infusion unit 112 to the skin S (FIG. 2) of the user. The handle 296 extends outwardly from the first base side 298. In one example, the handle 296 includes a cutout 310, a leg 312 and an introducer bore 314. The cutout 310 transitions the handle 296 from the recessed midsection 302 to the leg 312, and defines a ledge 310a. The ledge 310a is coupled to and in contact with the hub 146 of the outer housing 130 when the needle hub 152 is coupled to the infusion unit 112. The leg 312 includes a surface 312a, which contacts one of the bases 162 of one of the retaining flanges 148 to assist in coupling the infusion unit 112 to the user. The introducer bore 314 extends through the handle 296 from a first handle end 296a to a second handle end 296b. The introducer bore 314 enables the introducer pin 292 to be removably received within the handle 296. When the hub base 294 is coupled to the infusion unit 112, the introducer bore 314 is coaxially aligned with the needle bore 178 to enable the introducer pin 292 to pass through the needle bore 178 and the cannula 142 to insert the cannula 142 into the anatomy. The introducer bore 314 may have varying diameters along the introducer bore 314 from the first handle end 296a to the second handle end 296b that correspond to the diameter of the introducer pin 292. It should be noted, however, that the introducer bore 314 may have any desired shape that enables the introducer pin 292 to pass therethrough.

The introducer pin 292 is used by the user to couple the cannula 142 to the body of the user. The introducer pin 292 may be composed of a biocompatible metal or metal alloy, and is substantially solid or uncannulated. In one example, the introducer pin 292 includes a tip 316 and an optional graspable portion 318. The tip 316 is pointed or sharp for piercing the skin of the user. In one example, the tip 316 of the introducer pin 292 comprises, but is not limited to, a conical pointed tip, a beveled pointed tip or a trocar tip. The graspable portion 318 may provide a grip surface for the user. While the graspable portion 318 is shown as an annular thickened portion of the introducer pin 292, the graspable portion 318 may have any desired shape. In this example, the graspable portion 318 cooperates with a reduced diameter 314a of the introducer bore 314 to inhibit a further advancement of the tip 316 within the body of the user. Stated another way, the graspable portion 318 cooperates with the introducer bore 314 to limit an advancement of the introducer pin 292 into the user. It should be noted that other techniques may be employed to limit an amount of advancement of the tip 316 of the introducer pin 292 into the user. In addition, it should be noted that the introducer pin 292 may be formed with the needle hub 152, via molding, for example, and in this embodiment, the introducer pin 292 may not include the graspable portion 318. In certain embodiments, with reference to FIG. 3, the needle hub 152, the introducer pin 292, the infusion unit 112, the connector assembly 114 and the tube 110 are a kit 330, for fluidly coupling the fluid infusion device 102 (FIG. 1) to the user.

Figure 9:
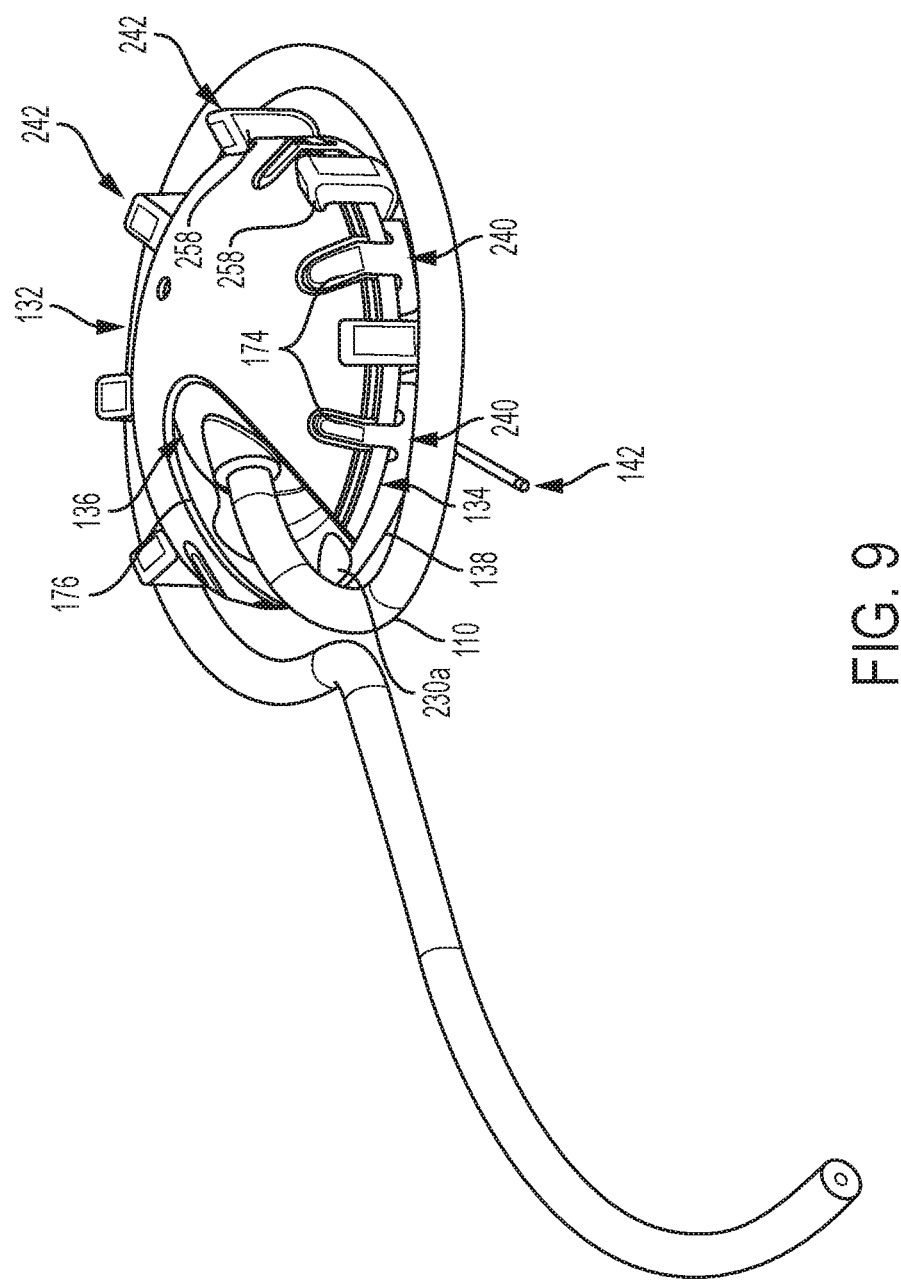
FIG. 9 is a perspective view of the infusion unit of FIG. 2, in which the outer housing is removed for clarity.

In order to assemble the infusion unit 112 and couple the tube 110 to the infusion unit 112, in one example, with the mount 138 and biasing member 134 formed, the biasing member 134 is positioned within the mount 138 and is retained by the projections 240 substantially about a perimeter of the biasing member 134. With the movable needle mount 136 formed, the first end 116 of the tube 110 is fixedly coupled to the tube receiving portion 200 of the movable needle mount 136 (FIG. 8). Generally, prior to fixedly coupling the tube 110 to the movable needle mount 136, the connector assembly 114 is coupled to the second end 118 of the tube 110. The movable needle mount 136 with the tube 110 attached is positioned onto the biasing member 134 such that the ledge 224 contacts the relief 192a of the biasing member 134. With the inner housing 132 formed, the inner housing 132 is snapped into the mount 138 such that the movable needle mount 136 and the biasing member 134 are sandwiched between the mount 138 and the inner housing 132 and a portion of the tube 110 extends through the clearance aperture 176. In this regard, with reference to FIG. 9, generally, each of the projections 240 are received in a respective one of the coupling slots 174 of the inner housing 132, and the hook 258 of each of the snap fingers 242 is engaged with the outer surface 170 of the inner housing 132. With reference back to FIG. 3, with the outer housing 130 formed, the outer housing 130 is positioned about the inner housing 132 and a portion of the tube 110 is received within the retaining recess 166 such that the portion of the tube 110 extends substantially about a circumference of the outer housing 130 near the perimeter of the outer housing 130. With the coupling device 140 formed, the mounting layer 270 is fixedly coupled to the second mount surface 232 and the surface 162b of each base 162 of the retaining flanges 148. The tube 110 may be coupled to the infusion unit 112 with the in-line connector 110b and the connector assembly 114 coupled to the tube 110 such that once the tube 110 is coupled to the assembled infusion unit 112, the infusion set 104 is formed.

In one example, with the infusion set 104 assembled, the hub body 290 of the needle hub 152 is coupled to the infusion unit 112 and the introducer pin 292 is coupled to the needle hub 152 for packaging and distribution to a user. Once received by a user, the user may remove the pre-assembled infusion set 104 out of the packaging. The user connects the infusion set 104 to the fluid reservoir of the fluid infusion device 102 and the user activates the fluid infusion device 102 to prime the infusion set 104. In certain instances, the user may prime a portion of the tube 110 coupled to the fluid infusion device 102 up to the in-line connector 110b, couple a portion of the tube 110 coupled to the infusion unit 112 to the remainder of the tube 110 at the in-line connector 110b, and once connected, activate the fluid infusion device 102 to fill/prime the rest of the tube 110 and the infusion unit 112.

The user may clean the insertion site on the skin S of the user with alcohol. With the insertion site prepared, the user may remove the backing 274. With the backing 274 removed, the user may manipulate the hub body 290, via the handle 296, to position the infusion unit 112 onto the skin S (FIG. 2) of the user. In other embodiments, the user may manipulate a quick insertion device to position the infusion unit 112 on the skin S of the user. With the infusion unit 112 positioned on the skin S of the user, the introducer pin 292 is inserted into the introducer bore 314 such that the tip 316 of the introducer pin 292 extends through the cannula 142 and pierces the skin S of the user to insert the second cannula end 282 of the cannula 142 into the body of the user. With the cannula 142 inserted into the body of the user, the infusion unit 112 is in the installed state. With the infusion unit 112 installed, the needle hub 152 is uncoupled from the infusion unit 112, which removes the introducer pin 292 from the user and leaves the infusion unit 112 coupled to or installed on the user. In the installed state, the infusion unit 112 provides a fluid flow path from the fluid reservoir associated with the fluid infusion device 102 (FIG. 1) into the body of the user. The user may smooth out the adhesive layer 272, as needed, once the infusion unit 112 is the installed state.

It will be understood that the infusion unit 112 of the infusion set 104 described with regard to FIGS. 1-9 may be configured differently to provide a fluid flow path from the fluid infusion device 102 to the body of the user. In one example, with reference to FIG. 10, an infusion unit 500 for the infusion set 104 is shown. As the infusion unit 500 includes components that are substantially similar to or the same as the infusion unit 112 discussed with regard to FIGS. 1-9, the same reference numerals will be used to denote the same or similar features.

Figure 11:
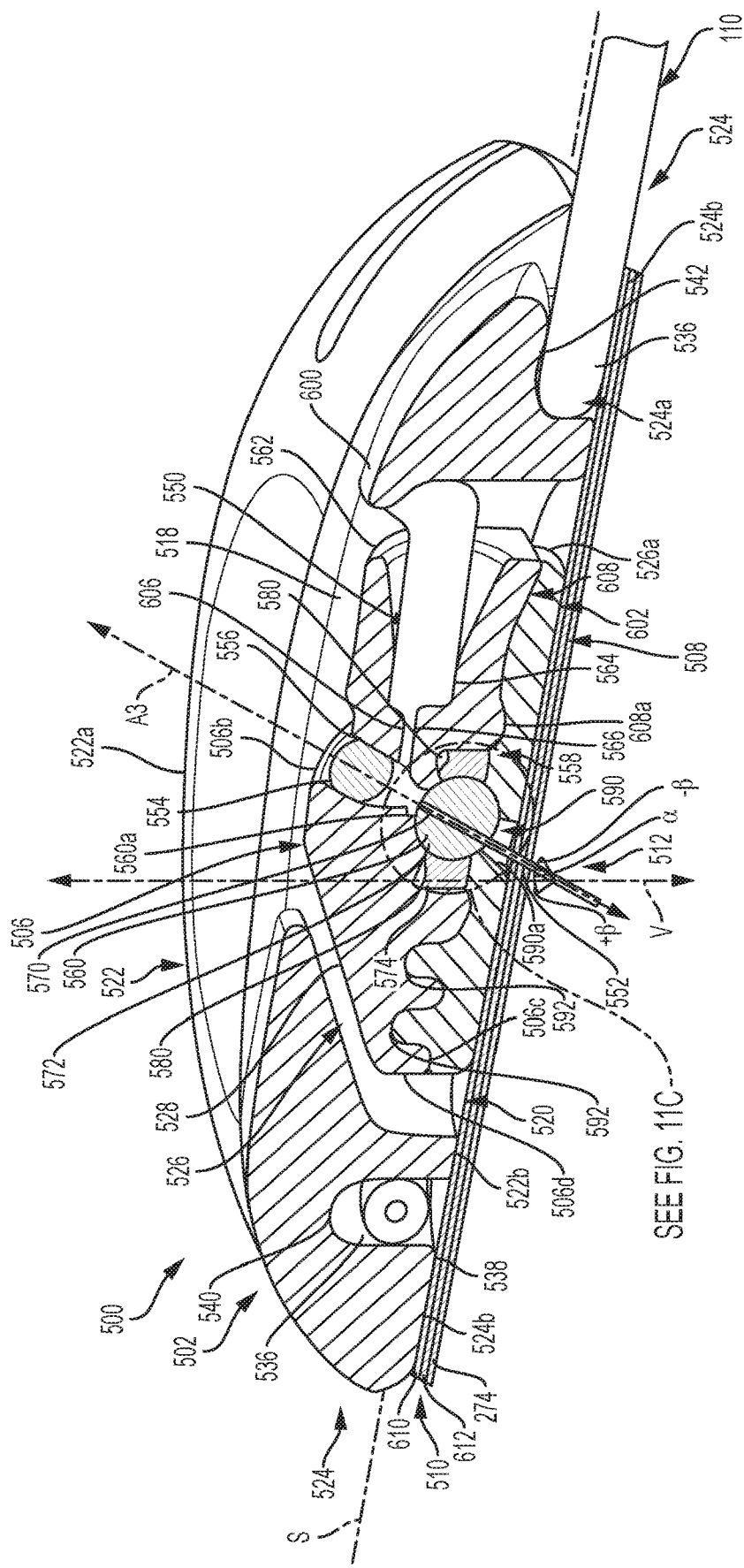
FIG. 11 is a cross-sectional view of the infusion unit of FIG. 10, taken along line 11-11 of FIG. 10, in which the introducer pin is removed for clarity.

With reference to FIG. 11, the infusion unit 500 of the infusion set 104 is shown installed onto a skin S of a user. The infusion unit 500 delivers fluid from the fluid reservoir associated with the fluid infusion device 102 (FIG. 1) received via the tube 110 into the body of the user. In one example, the infusion unit 500 includes a first or outer housing 502, a second or inner housing 506, a mount 508, a coupling device 510 and a needle or metal cannula 512.

The outer housing 502 surrounds the inner housing 506 and the mount 508. Generally, the outer housing 502 circumscribes the inner housing 506 and the mount 508, but is not coupled to the inner housing 506 or the mount 508. The outer housing 502 is uncoupled from or discrete from the inner housing 506 and the mount 508 to provide strain relief to the first end 116 of the tube 110. In this regard, by being disjoined from the inner housing 506 and the mount 508, any strain imparted to the tube 110 will be dissipated by the outer housing 502, which reduces a likelihood of the first end 116 of the tube 110 being uncoupled from the inner housing 506. In one example, the outer housing 502 is composed of a polymer-based material, including, but not limited to, polypropylene, silicone or a thermoplastic elastomer. The outer housing 502 may be formed through molding, casting, printing, etc. The outer housing 502 is generally concave, however, the outer housing 502 may have any desired shape.

In this example, the outer housing 502 includes a slot 518, a central aperture 520, an annular hub 522 and a plurality of retaining flanges 524. The slot 518 is in communication with the central aperture 520, and is elongated to enable an installation of the infusion unit 500. In one example, the slot 518 is configured to mate with a needle hub, similar to the needle hub 152, to assist the user in installing the infusion unit 500. The slot 518 is defined through a first hub surface 522a of the hub 522. The central aperture 520 is defined through a second hub surface 522b of the hub 522 of the outer housing 502. The central aperture 520 is sized to surround the inner housing 506 and the mount 508. In one example, the central aperture 520 includes a tapered wall 526. The tapered wall 526 is defined to be proximate a tapered wall 528 of the inner housing 506. The incline or taper of the tapered wall 526 of the outer housing 502 is complementary to the incline or taper of the tapered wall 528 of the inner housing 506 to enable a transfer of forces, such as compressive forces applied to the outer housing 502, between the outer housing 502 and the inner housing 506. In on example, a clearance is defined between the inner housing 506 and the outer housing 502 such that during normal usage the inner housing 506 does not contact the outer housing 502.

Figure 10:
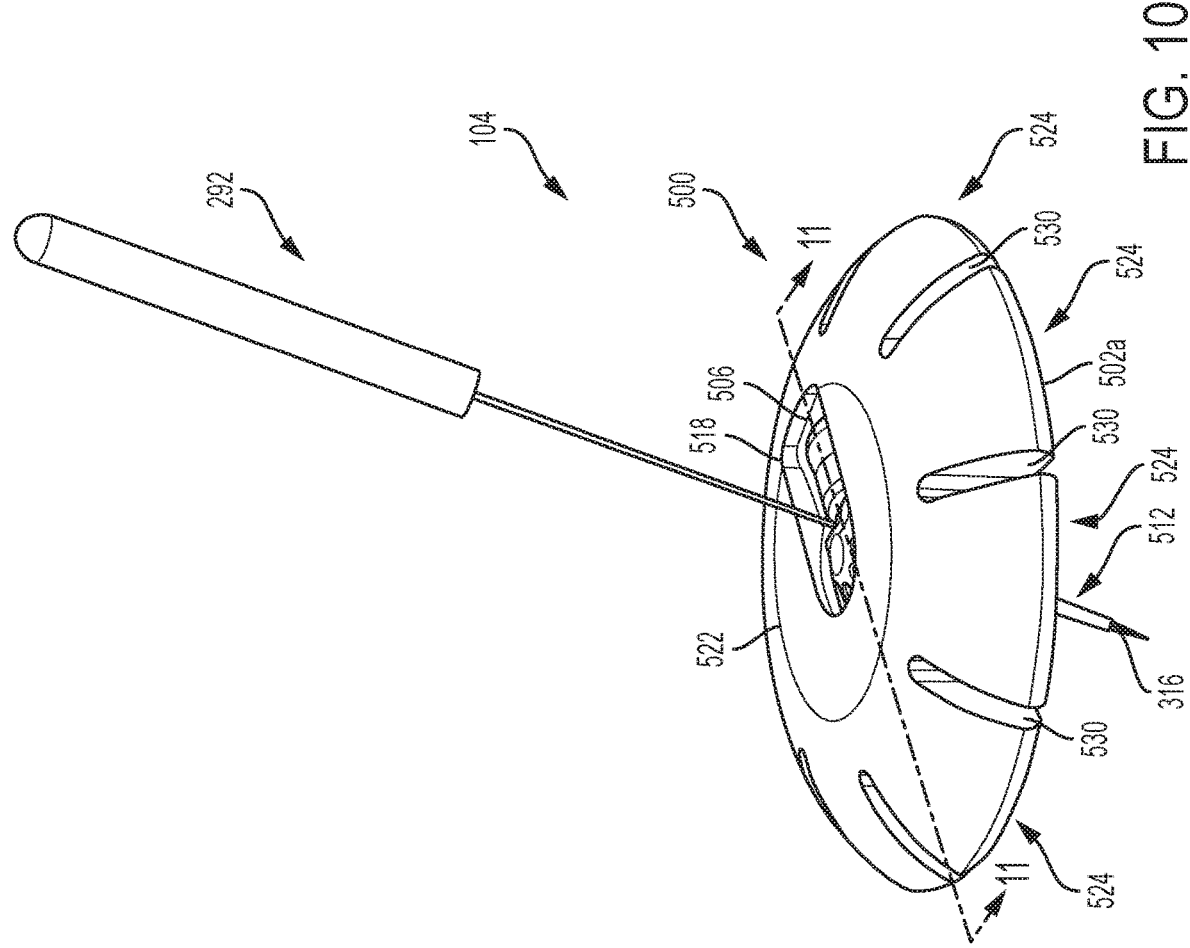
FIG. 10 is an environmental perspective view of an exemplary infusion unit with a pivotable metal cannula and strain relief for use with the infusion set of FIG. 1, which shows an installation of the infusion unit with a removable introducer pin.
Figure 11A:
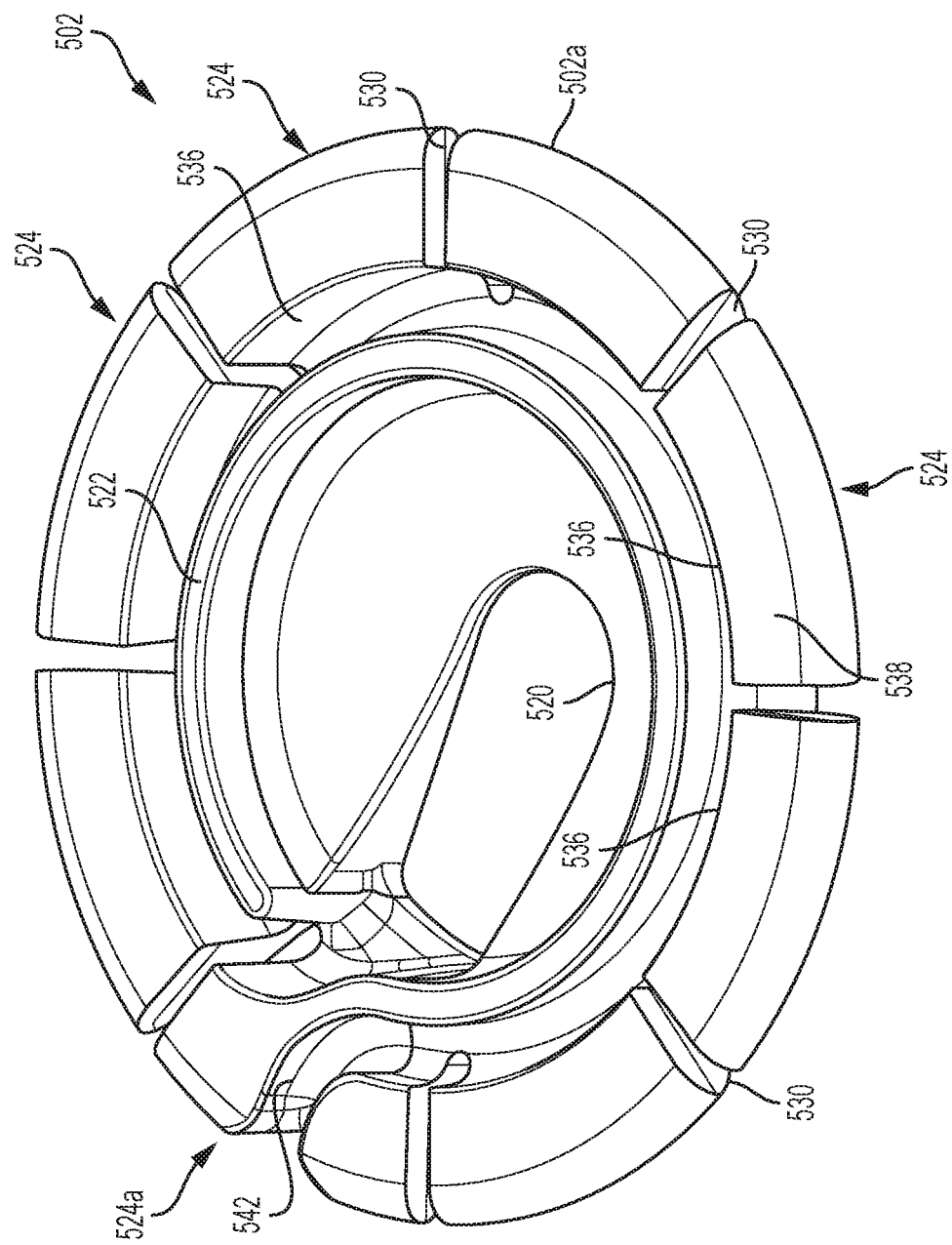
FIG. 11A is a bottom perspective view of an outer housing associated with the infusion unit of FIG. 10.

The hub 522 may be coupled to a needle hub to install the infusion unit 500 on a body of a user. In one example, the hub 522 surrounds the central aperture 520 and is interconnected to each of the plurality of retaining flanges 524. The plurality of retaining flanges 524 are spaced apart about a perimeter or circumference of the hub 522. In one example, with reference to FIG. 10, each of the plurality of retaining flanges 524 is separated by a respective one of a plurality of slots 530 defined from an outer periphery or perimeter 502a of the outer housing 502 to the hub 522. In one example, the outer housing 502 includes 8 retaining flanges 524, however, the outer housing 502 may include any number of retaining flanges, such as 4 to 16. With to FIGS. 11 and 11A, each of the retaining flanges 524 includes a retaining recess 536. The retaining recess 536 is substantially U-shaped, and is defined through each of the retaining flanges 524 from a first flange surface 538 toward a second flange surface 540 (FIG. 11). Each of the retaining recesses 536 are sized and shaped to receive a portion of the tube 110 to secure the tube 110 to the outer housing 130. Generally, the retaining recesses 536 of the retaining flanges 524 cooperate to enable the tube 110 to be positioned about a circumference of the outer housing 502 near the outer perimeter 502a of the outer housing 130 (FIG. 10). Each of the retaining flanges 524 is substantially the same, except for the retaining flange 524a. The retaining flange 524a includes a cutout 542 defined through the first flange surface 538 that is in communication with the retaining recess 536. The cutout 542 enables a portion of the tube 110 to pass through the retaining flange 524a.

Figure 12:
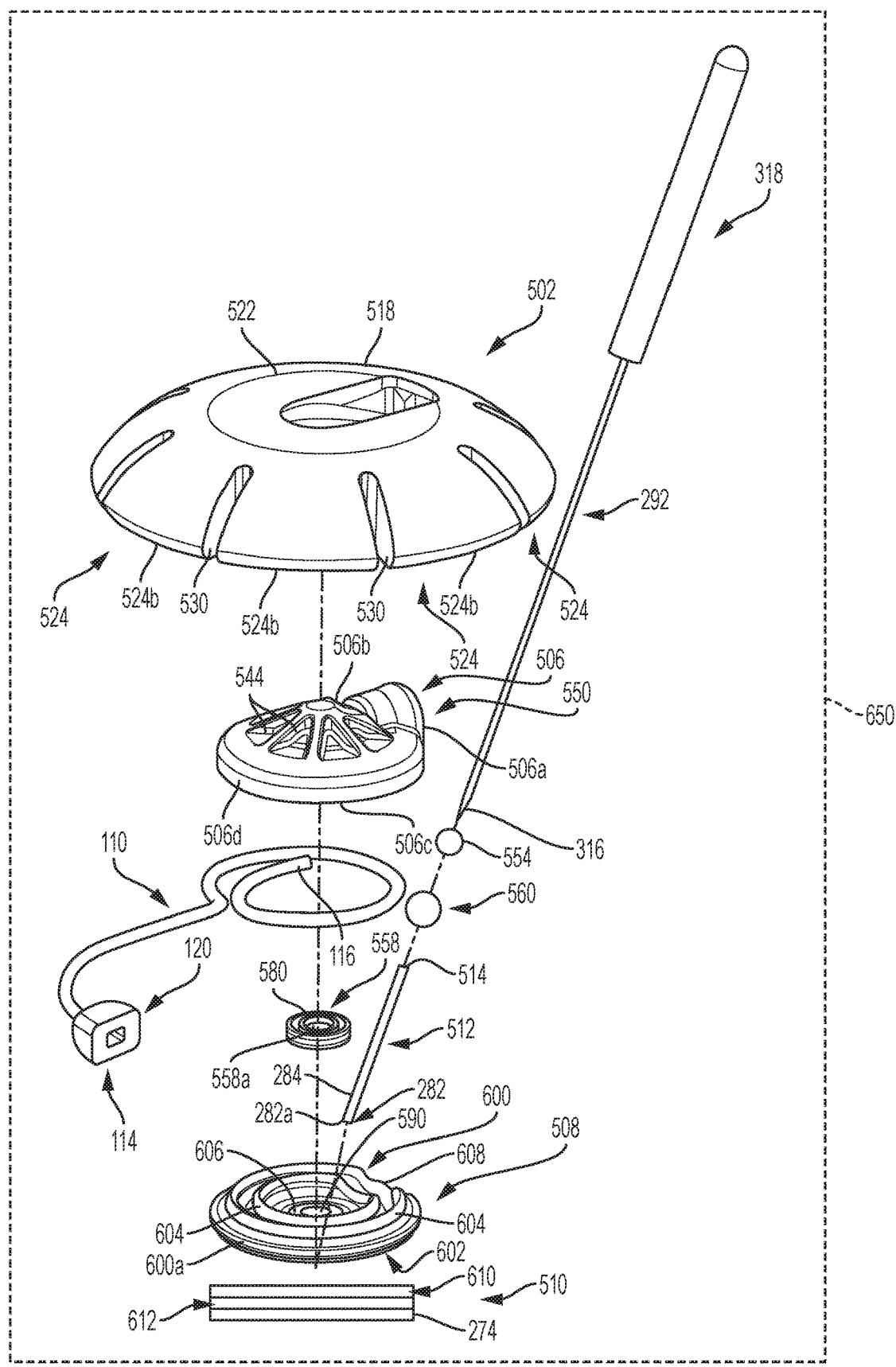
FIG. 12 is an exploded view of a kit for the infusion set, which includes the infusion unit of FIG. 10.

As will be discussed, with reference to FIG. 11, an articulation member enables the cannula 512 to move or pivot relative to the inner housing 506, and thus, the outer housing 502 and the infusion unit 500. In one example, the articulation member is received within the inner housing 506 enables the cannula 512 to move or pivot when the skin S of the user moves or when an external force or load is applied to the infusion unit 500. In one example, the inner housing 506 is composed of a polymer-based material, including, but not limited to, polypropylene, silicone or a thermoplastic elastomer. The inner housing 506 may be formed through molding, casting, printing, etc. With reference to FIG. 12, the inner housing 506 is substantially annular, however, the inner housing 506 may have any desired shape. In one example, with reference back to FIG. 11, the inner housing 506 includes a tube receiving portion 550, a needle guide 552, a septum 554, a septum bore 556, a seal 558 and an articulation member 560. In one example, the inner housing 506 is substantially round, but the inner housing 506 may have any desired shape.

The tube receiving portion 550 is substantially cylindrical, and is sized to receive the first end 116 of the tube 110 and to cooperate with the tube 110 to define the fluid flow path to the user. The tube receiving portion 550 is defined at a first needle mount end 506a of the inner housing 506. The tube receiving portion 550 includes a first end 562 and an opposite second end 564. The first end 562 receives a portion of the tube 110 adjacent to the first end 116. The first end 562 may have a diameter, which is larger than a diameter of the second end 564. In this example, the first end 562 is flared outward toward the first needle mount end 506a of the inner housing 506. The outward flare of the first end 562 defines a pocket, which may receive an adhesive or other coupling mechanism for securing the tube 110 to the tube receiving portion 550. The second end 564 is fixedly couple to the first end 116 of the tube 110, and includes an outlet 566. Generally, the first end 116 of the tube 110 is fixedly coupled to the second end 564 via any suitable technique, including, but not limited to, adhesives, ultrasonic welding, etc. The outlet 566 defines a fluid flow path from the first end 116 of the tube 110 to the cannula 512. The outlet 566 is in fluid communication with the needle guide 552 to direct the fluid from the fluid reservoir of the fluid infusion device 102 (FIG. 1) into the body of the user.

The needle guide 552 includes an inlet 570, an articulation member bore 572, and a seal bore 574. The inlet 570 is in fluid communication with the outlet 566 to receive the fluid. In one example, the inlet 570 is substantially funnel shaped to direct the fluid from the outlet 566 into the cannula 512. The articulation member bore 572 is adjacent to or proximate the inlet 570 and is in communication with the inlet 570 and the seal bore 574. The articulation member bore 572 is substantially spherical and is sized to receive the articulation member 560. The articulation member bore 572 enables the articulation member 560 to move within the articulation member bore 572 based on a movement of the cannula 512, for example. The seal bore 574 surrounds a portion of the articulation member bore 572. The seal bore 574 is substantially cylindrical, and is sized to receive the seal 558. Generally, the seal 558 is fixedly coupled to the seal bore 574, via adhesives, ultrasonic welding, etc.

The septum 554 is coupled to the septum bore 556. In one example, the septum 554 is fixedly coupled to the septum bore 556 via adhesives, ultrasonic welding, press-fit, etc. With reference to FIG. 12, the septum 554 is generally spherical; however, the septum 554 may have any desired shape. The septum 554 serves as a barrier to prevent the ingress and egress of fluids into the fluid flow path defined by the tube 110 and the cannula 512 within the infusion unit 500. The septum 554 is pierceable by the introducer pin 292 to enable the user to install the infusion unit 500. With reference back to FIG. 11, the septum bore 556 is defined through a first needle mount surface 506b and is in communication with the inlet 570. The septum bore 556 is sized and shaped to receive the septum 554. In one example, the septum bore 556 is substantially cylindrical and the septum 554 has a diameter that is greater than a diameter of the septum bore 556 to create a seal between the septum 554 and the septum bore 556.

The seal 558 prevents the egress of the fluid from the inlet 570. In one example, with reference to FIG. 12, the seal 558 is substantially annular. An outer perimeter 558a of the seal 558 is fixedly coupled to the seal bore 574, via adhesives, ultrasonic welding, etc. The seal 558 is generally composed of a biocompatible polymer-based material, including, but not limited to, an elastomer, silicone, etc. In one example, the seal 558 includes a central seal bore 580. The central seal bore 580 is cylindrical, and is sized to surround a portion of the articulation member 560, as shown in FIG. 11. The central seal bore 580 enables the articulation member 560 to move while inhibiting the egress of fluid from the inner housing 506.

The articulation member 560 is received between the inner housing 506 and the mount 508. The articulation member 560 is movable relative to the inner housing 506 and the mount 508 to enable the cannula 512 to move relative to the infusion unit 500. The articulation member 560 is offset from a central vertical axis V that is defined through the infusion unit 500. In this example, the cannula 512 is fixedly coupled to the articulation member 560. In one example, the cannula 512 is fixedly coupled to the articulation member 560 via adhesives, ultrasonic welding, overmolding, press-fit, etc. Generally, with reference to FIG. 11C, a first cannula end 514 is coupled to the articulation member 560 so as to be coincident with an exterior surface 560a of the articulation member 560. Alternatively, the first cannula end 514 may be recessed within the articulation member 560. As a further alternative, the first cannula end 514 may be flared, similar to the first cannula end 280 of the cannula 142 of FIGS. 1-9. The articulation member 560 is spherical, and is composed of a polymer-based material, including, but not limited to polypropylene, polycarbonate, polyester, acrylonitrile butadiene styrene (ABS), acetal, polyether ether ketone (PEEK). The articulation member 560 may be formed by molding, printing, casting, etc. In addition, the articulation member 560 may be formed by overmolding the articulation member 560 onto the cannula 512.

Figure 11B:
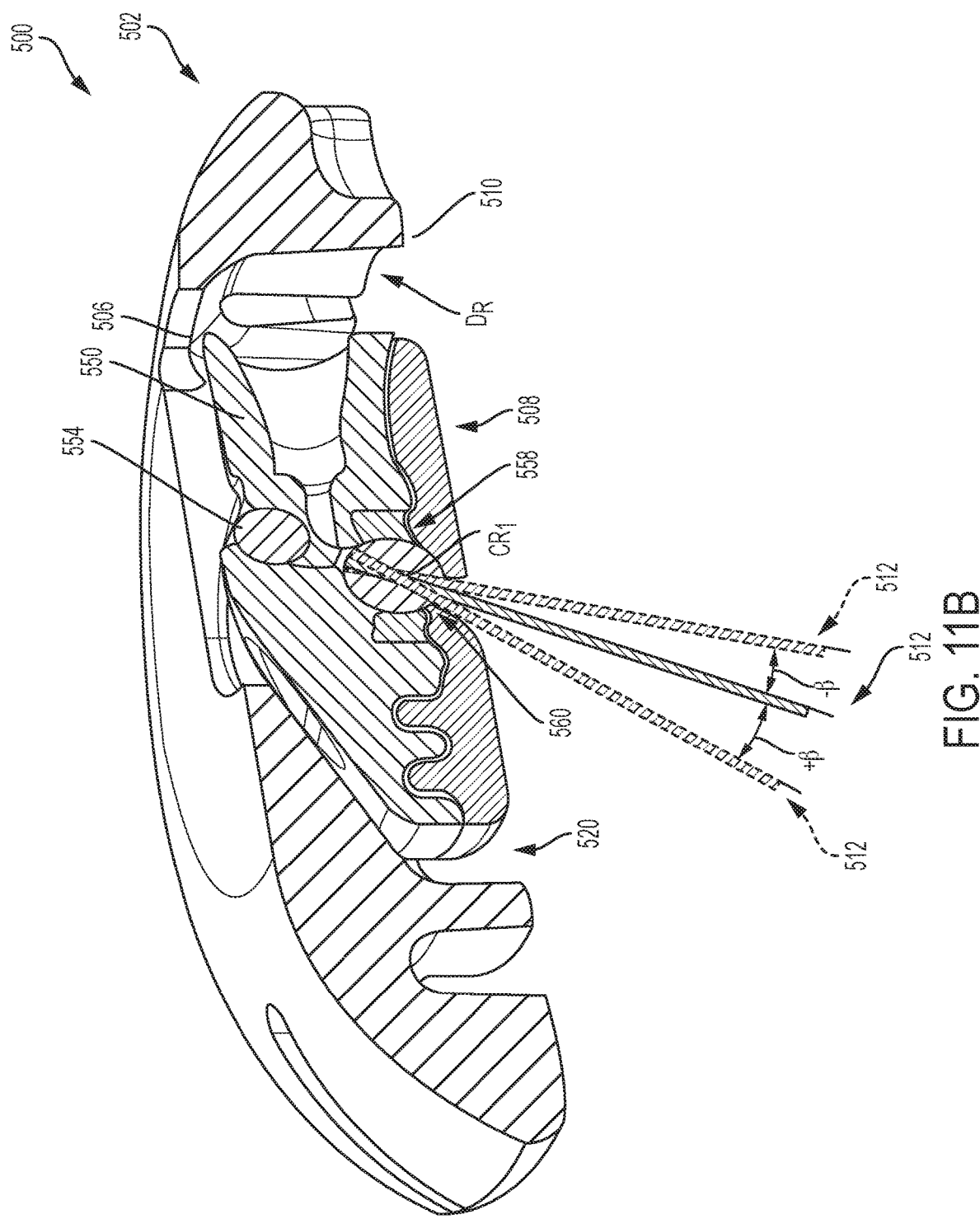
FIG. 11B is a schematic cross-sectional view of the infusion unit of FIG. 10, taken from the perspective of line 11-11 of FIG. 10, in which the introducer pin and the coupling device are removed for clarity, and a cannula of the infusion unit is pivoted about a positive angle and a negative angle.

With reference to FIG. 11, the articulation member 560 moves or pivots along the cooperating spherical surface of the articulation member bore 572. Generally, the articulation member 560 cooperates with the inner housing 506 to enable the cannula 512 to move or pivot relative to the angle α defined between the vertical axis V of the infusion unit 500 and the axis A3 through the center line of the cannula 512. In one example, the angle α is about 10 degrees to about 45 degrees. In one example, the articulation member 560 is movable or pivotable the angle β relative to the angle α. In this example, angle β is about ±5 degrees to about ±20 degrees relative to the angle α. Generally, the articulation member 560 is coupled to the infusion unit 500 such that a center of rotation CR1 of the cannula 512 is located near the entry point of the cannula 512 into the skin S of the user within about ±2.5 millimeters (mm). Generally, in one example, the center of rotation CR1 is above the skin S of the user, but within about ±2.5 millimeters (mm). It should be noted that the movement of the cannula 512 is conical, and thus, the movement of the cannula 512 about the angle β is a conical movement in and out of the plane shown in FIG. 11B. In this example, the rotation of the cannula 512 about the vertical axis V of the infusion unit 500 is symmetric and conical, however, it should be understood that the angle of rotation of the cannula 512 may be asymmetrical, if desired. As shown in FIG. 11B, a movement of the inner housing 506 in a direction DR may cause the cannula 512 to rotate a negative angle β relative to the vertical axis V of the infusion unit 500. Similarly, a movement of the inner housing 506 in a direction opposite the direction DR may cause the cannula 512 to rotate a positive angle β relative to the vertical axis V of the infusion unit 500.

In one example, a bore 590 of the mount 508 may define a range of motion of the cannula 512. In this example, a sidewall 590a of the bore 590 may contact the cannula 512 to stop the further movement of the cannula 512, and thus, the articulation member 560 relative to the inner housing 506 and the mount 508. In one example, the sidewall 590a may include an incline on one side. It should be noted, however, that the sidewall 590a may include the incline about an entirety of the sidewall 590a or that the sidewall 590a may be substantially straight.

Figure 12A:
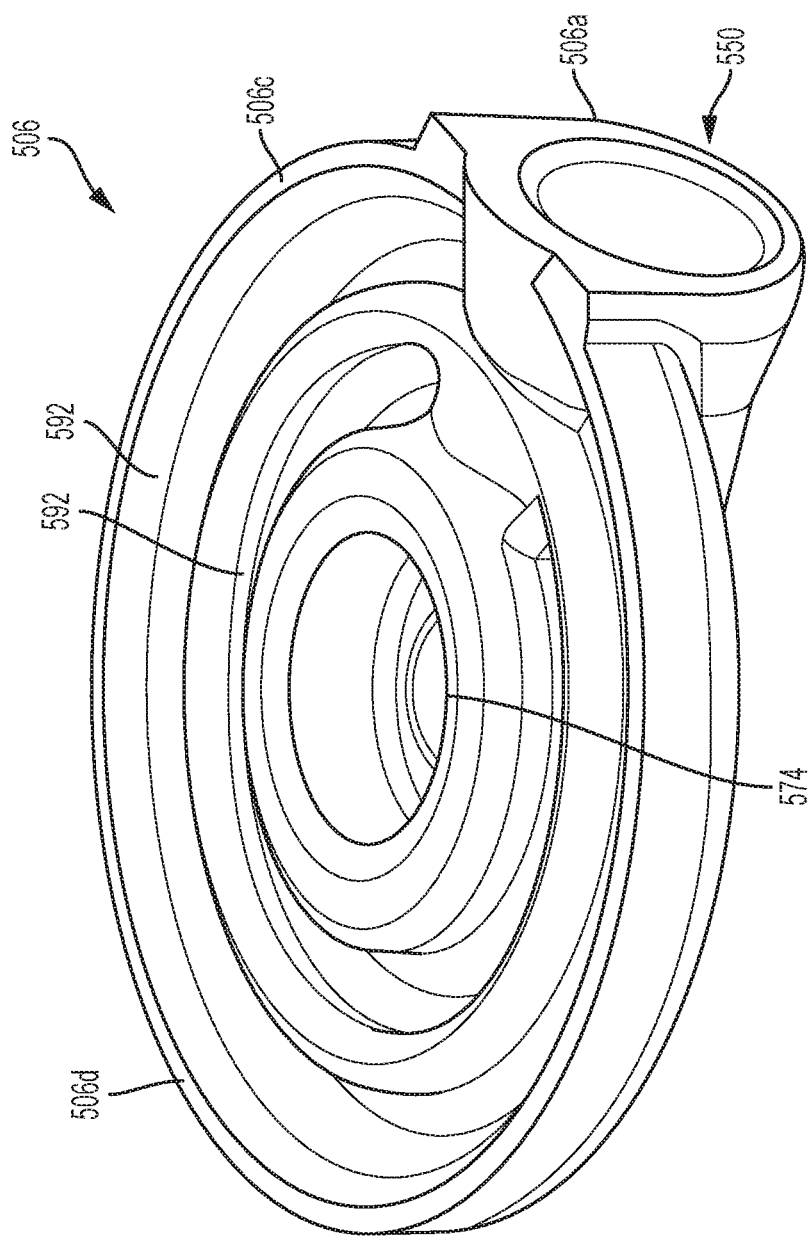
FIG. 12A is a bottom perspective view of an inner housing of the infusion unit of FIG. 10.

The inner housing 506 is fixedly coupled to the mount 508. In one example, the inner housing 506 includes a plurality of mount coupling features or grooves 592, which extend about a portion of a circumference of the inner housing 506. In this example, with reference to FIG. 12A, the inner housing 506 includes two grooves 592, which are spaced apart to define dispensing channels for dispensing an adhesive to couple the inner housing 506 to the mount 508. However, it should be noted that in other embodiments, the grooves 592 may be employed to define an ultrasonic weld. Generally, with reference to FIG. 12, each of the grooves 592 are defined from a second needle mount surface 506c toward the first needle mount surface 506b. The first needle mount surface 506b is opposite the second needle mount surface 506c, and the first needle mount end 506a is opposite a second needle mount end 506d. The first needle mount surface 506b may also include a plurality of substantially triangular reliefs 594 spaced apart about a circumference of the inner housing 506. The reliefs 594 assist in forming the inner housing 506.

The mount 508 is coupled to the coupling device 510 and to the inner housing 506. The mount 508 is substantially circular; however, the mount 508 may have any desired shape. In one example, the mount 508 is composed of a polymer-based material, including, but not limited to, polypropylene, silicone or a thermoplastic elastomer. The mount 508 may be formed through molding, casting, printing, etc. The mount 508 includes a first mount surface 600, a second mount surface 602 opposite the first mount surface 600 and the bore 590.

Figure 12B:
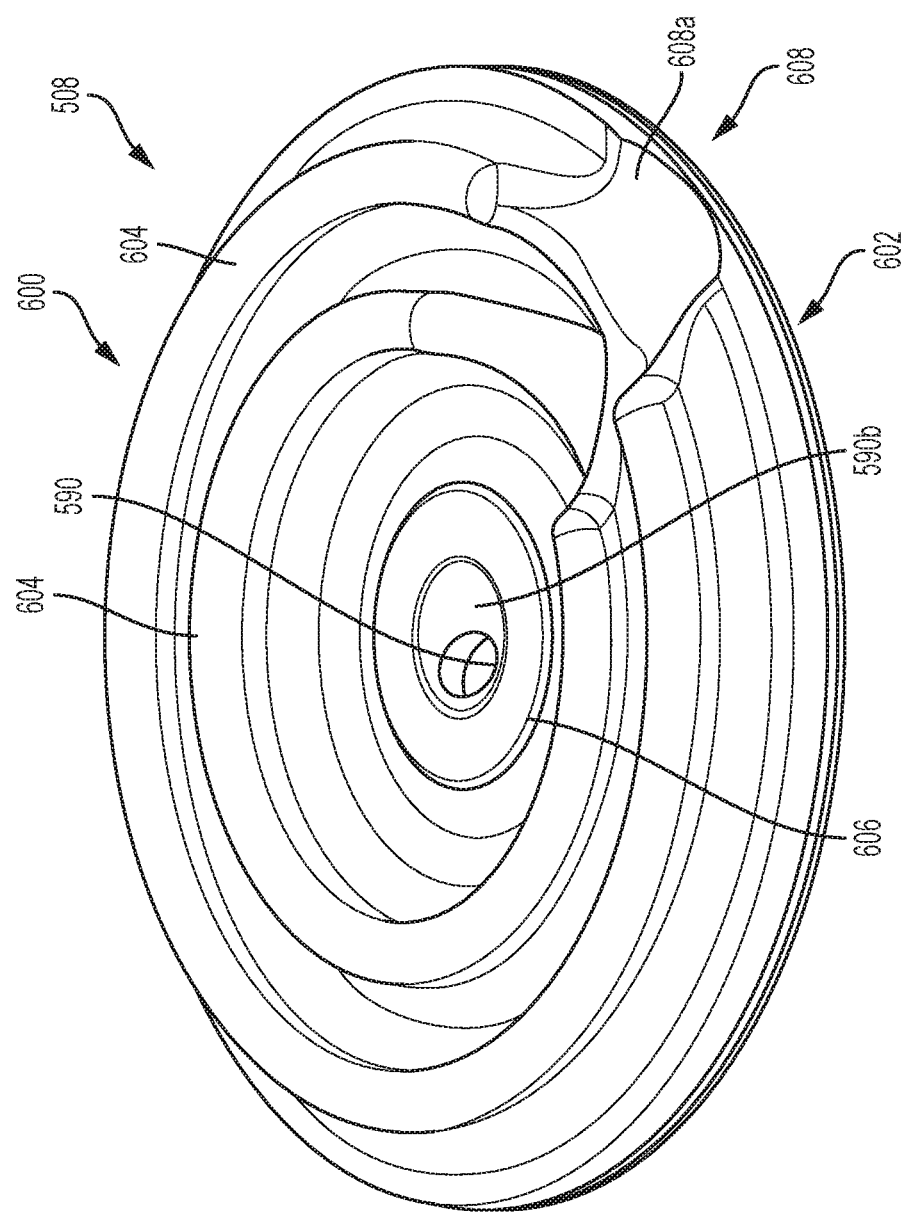
FIG. 12B is a top perspective view of a mount of the infusion unit of FIG. 10.

With reference to FIG. 12B, the first mount surface 600 includes a plurality of ribs 604, a seal interface 606 and a tube receiving interface 608. The plurality of ribs 604 extend axially upward from the first mount surface 600 near the perimeter or outer circumference 600a of the first mount surface 600. In one example, the mount 508 includes two circular ribs 604, which extend about a portion of the first mount surface 600 and are each intersected by the tube receiving interface 608. Each of the circular ribs 604 are received in a respective one of the grooves 592 of the inner housing 506 to couple the inner housing 506 to the mount 508. In one example, the ribs 604 are coupled to the grooves 592 via adhesives; however, the ribs 604 may be coupled to the grooves 592 via ultrasonic welding, snap-fit, etc.

The seal interface 606 cooperates with the inner housing 506 to retain the seal 558. In one example, the seal interface 606 is a surface, which is defined radially inward from the ribs 604. The seal interface 606 is also generally defined about the bore 590. In one example, a concave recess 590b is defined about the bore 590 proximate the seal interface 606 to provide an articulation surface for the articulation member 560. The tube receiving interface 608 has a shape that corresponds to an exterior surface of the tube receiving portion 550 of the mount 508. In one example, the tube receiving interface 608 is substantially curved, and includes a concave relief 608a. The concave relief 608a receives part of the exterior surface of the tube receiving portion 550 of the inner housing 506 to aid in coupling the inner housing 506 to the mount 508.

The second mount surface 602 is substantially flat or planar. With reference to FIG. 11, the second mount surface 602 is coupled to the coupling device 510. The bore 590 is defined through the first mount surface 600 and the second mount surface 602. The bore 590 is defined through the mount 508 so as to extend substantially along the axis A3, which is transverse or oblique to the vertical axis V. The cannula 512 extends through the bore 590.

With reference to FIG. 11, the coupling device 510 removably couples or secures the mount 508 of the infusion unit 500 to the body of the user. In one example, with reference to FIG. 13, the coupling device 510 includes a mounting layer 610, an adhesive layer 612 and the backing 274. It should be noted that the mounting layer 610 and the adhesive layer 612 are illustrated herein as having a nominal thickness, but that the mounting layer 610 and the adhesive layer 612 could have any suitable thickness as necessary for the manufacture of the coupling device 510. The mounting layer 610 and adhesive layer 612 may be separately or integrally formed. The mounting layer 610 couples or fixedly attaches the adhesive layer 612 to the second mount surface 602 of the mount 508 and to a surface 524b of each of the retaining flanges 524. The mounting layer 610 may be coupled or secured to the second mount surface 602 of the mount 508 and the surface 524b of the retaining flanges 524 through any suitable technique, including, but not limited to, ultrasonic welding. Generally, the mounting layer 610 is coupled to substantially the entirety of the second mount surface 602 of the mount 508 and a surface 524b associated with the retaining flanges 524 of the outer housing 502. Thus, in one example, the mounting layer 610 is fixedly coupled to the mount 508 and to the outer housing 502. It should be noted, however, that while the mounting layer 610 is illustrated herein as being defined over substantially an entire surface of the coupling device 510, the mounting layer 610 may be coupled to just a portion of the surface of the adhesive layer 612. For example, the mounting layer 610 may be coupled to the adhesive layer 612 so as to extend over a portion of the adhesive layer 612 that corresponds with the portion of the coupling device 510 that is coupled to the mount 508 and/or the outer housing 502. In other words, the mounting layer 610 may be sized to correspond to the size of the mount 508 and/or outer housing 502, and can have a shape that may be different than a shape of the adhesive layer 612.

The adhesive layer 612 enables the infusion unit 500 to be removably coupled to the body of the user. It should be noted that the use of the adhesive layer 612 is merely exemplary, as any suitable technique could be used to removably couple the infusion unit 500 to the user. In one example, the adhesive layer 612 is shown in greater detail. In this example, the adhesive layer 612 is annular; however, the adhesive layer 612 may include a plurality of petals, such as the plurality of petals 276. As the mounting layer 610 is shaped to correspond to the adhesive layer 612, in this example, the mounting layer 610 is also annular. The mounting layer 610 includes a bore 610a, which is sized to enable a portion of the cannula 512 to pass therethrough. The adhesive layer 612 also includes a bore 612a, which is also sized to enable a portion of the cannula 512 to pass therethrough. The backing 274 is coupled to at least a portion of the adhesive layer 612, and is removable to facilitate coupling the coupling device 140 to the user, as is generally known.

Figure 11C:
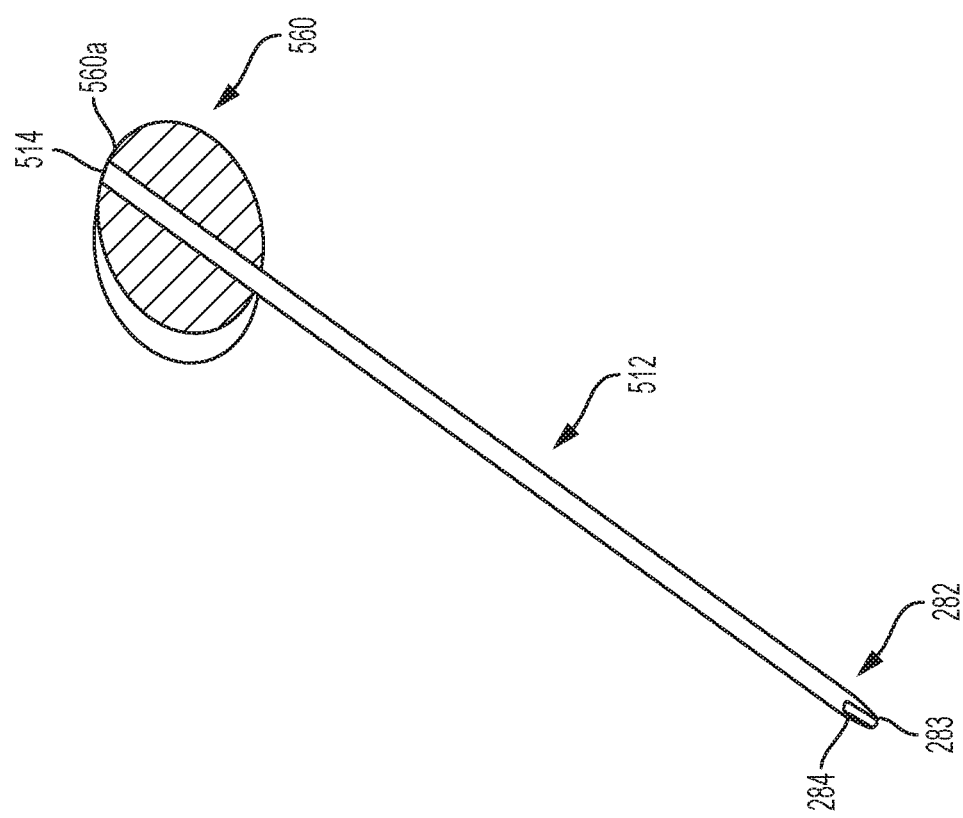
FIG. 11C is a detail cross-sectional view taken at 11C on FIG. 11, which illustrates the cannula coupled to an articulation member of the infusion unit of FIG. 10.

With reference to FIG. 11C, the cannula 512 delivers the fluid from the tube 110 into the body of the user. In this example, the cannula 512 is composed of a biocompatible metal or metal alloy, including, but not limited to, titanium, nickel-titanium alloy, titanium alloy, stainless steel, etc. It should be noted that the use of a cannula 512 composed of titanium, nickel-titanium alloy or titanium alloy results in the cannula 512 having increased flexibility when compared to a cannula 512 composed of a stainless steel. Thus, the use of titanium, nickel-titanium alloy or titanium alloy for the cannula 512 may provide the user with improved comfort. In one example, the cannula 512 has an outside diameter that is about or less than 30 gauge, and in one example, the cannula 512 comprises, but is not limited to, a 29 gauge cannula, a 29 gauge thin wall (29TW) cannula, a 29 gauge extra thin wall (29XTW), a 30 gauge, a 30 gauge thin wall (30TW) or a 30 gauge extra thin wall (30XTW). By reducing the thickness of the wall of the cannula 512 through the use of the thin wall or extra thin wall cannulas 512, an outside diameter of the introducer pin 292 may be increased relative to the outside diameter of the cannula 512, which results in less insertion strain when the cannula 512 follows the introducer pin 292 into the skin of the user. The use of the thin wall or extra thin wall cannulas 512 allow provides for a larger inner diameter for the cannula 512, which may reduce occlusions. The cannula 512 includes the first cannula end 514 and the opposite second cannula end 282. The cannula 512 includes the central needle bore 283, which extends from the first cannula end 514 to the second cannula end 282. In one example, the first cannula end 514 is substantially cylindrical.

The introducer pin 292 is used to insert the cannula 512 into the body of the user. In one example, the tip 316 of the introducer pin 292 pierces the skin S (FIG. 11) of the user to insert the cannula 512 into the body of the user. The graspable portion 318 may provide a grip surface for the user to manipulate the introducer pin 292. It should be noted that although not shown herein, the graspable portion 318 may be modified to integrate with an insertion aid device, including, but not limited to, a MiniMed Sil-serter®, MiniMed Quick-serter® each commercially available from Medtronic Minimed, Inc. of Northridge, Calif. or the like, to assist the user in inserting the cannula 142 at an angle into the skin. In certain embodiments, with reference to FIG. 12, the introducer pin 292, the infusion unit 500, the connector assembly 114 and the tube 110 are a kit 650, for fluidly coupling the fluid infusion device 102 (FIG. 1) to the user.

In order to assemble the infusion unit 500, in one example, with the mount 508 and the seal 558 formed, the seal 558 is positioned within the mount 508 on the seal interface 606. With the inner housing 506 formed, the first end 116 of the tube 110 is fixedly coupled to the tube receiving portion 550 of the inner housing 506 (FIG. 11). Generally, prior to fixedly coupling the tube 110 to the inner housing 506, the connector assembly 114 is coupled to the second end 118 of the tube 110. With the articulation member 560 and the cannula 512 formed, the cannula 512 is fixedly coupled to the articulation member 560 so as to extend through the articulation member 560. The articulation member 560 is coupled to the central seal bore 580 of the seal 558 such that the cannula 512 extends through the bore 590 of the mount 508. The septum 554 is inserted into the septum bore 556 of the inner housing 506, and the inner housing 506, with the tube 110 attached, is coupled to the mount 508 such that the ribs 604 are snap-fit into a respective one of the grooves 592 (FIG. 11).

Figure 14:
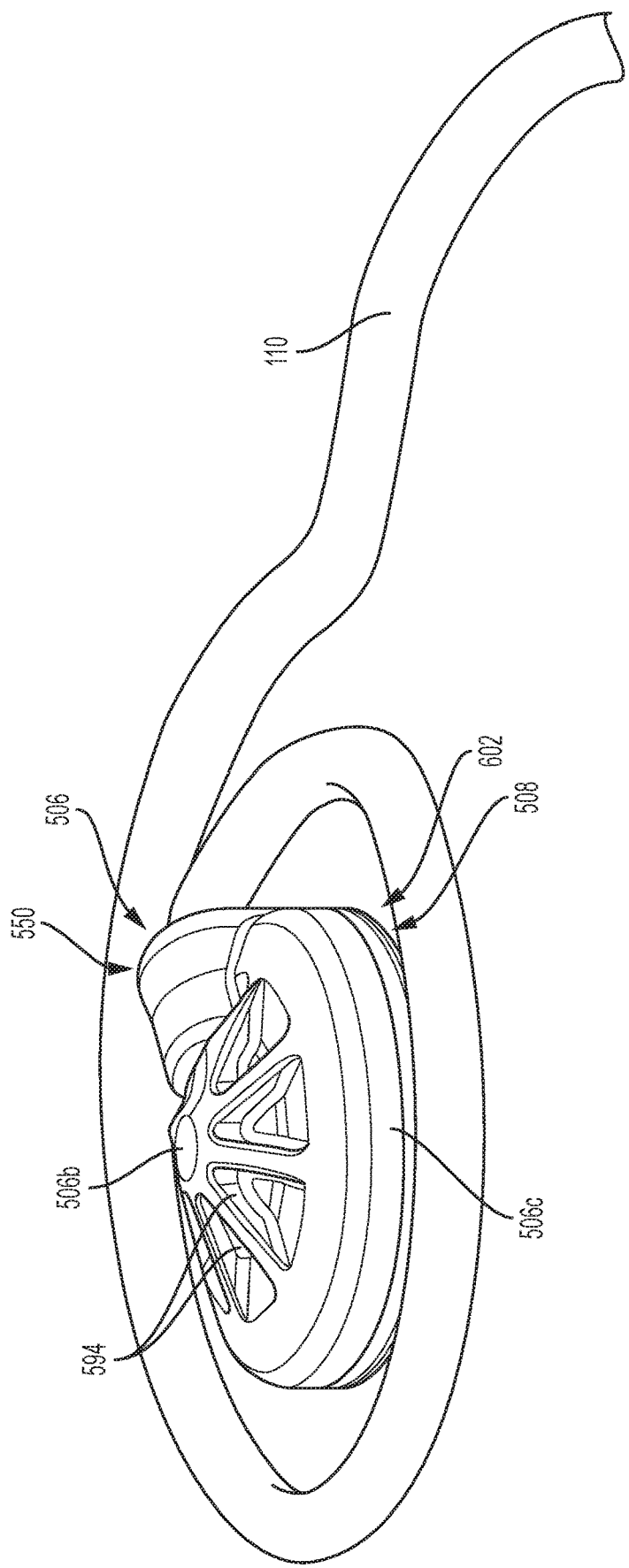
FIG. 14 is a perspective view of the infusion unit of FIG. 10, in which the outer housing is removed for clarity.

With reference to FIG. 14, the tube 110 may be positioned about the outer perimeter of the inner housing 506 and the mount 508. With the outer housing 502 formed, the outer housing 502 is positioned about the inner housing 506 and a portion of the tube 110 is received within the retaining recess 536 such that the portion of the tube 110 extends substantially about a circumference of the outer housing 502 near the perimeter 502a of the outer housing 502, as shown in FIG. 11. With the coupling device 510 formed, the mounting layer 610 is fixedly coupled to the second mount surface 602 and the surface 524b of each of the retaining flanges 524. The tube 110 may be coupled to the infusion unit 500 with the in-line connector 110b and the connector assembly 114 coupled to the tube 110 such that once the tube 110 is coupled to the assembled infusion unit 112, the infusion set 104 is formed.

In one example, with the infusion set 104 assembled, a needle hub is coupled to the infusion unit 500 and the introducer pin 292 is coupled to the needle hub for packaging and distribution to a user. Once received by a user, the user may remove the pre-assembled infusion set 104 out of the packaging. The user connects the infusion set 104 to the fluid reservoir of the fluid infusion device 102 and the user activates the fluid infusion device 102 to prime the infusion set 104. In certain instances, the user may prime a portion of the tube 110 coupled to the fluid infusion device 102 up to the in-line connector 110b, couple a portion of the tube 110 coupled to the infusion unit 500 to the remainder of the tube 110 at the in-line connector 110b, and once connected, activate the fluid infusion device 102 to fill/prime the rest of the tube 110 and the infusion unit 500.

The user may clean the insertion site on the skin S of the user with alcohol. With the insertion site prepared, the user may remove the backing 274. With the backing 274 removed, the user may manipulate the outer housing 502 via the needle hub coupled to the outer housing 502, for example, to position the infusion unit 500 onto the skin S (FIG. 2) of the user. In other embodiments, the user may manipulate a quick insertion device to position the infusion unit 500 on the skin S of the user. With the infusion unit 500 positioned on the skin S of the user, the introducer pin 292 is inserted into the septum bore 556 such that the tip 316 of the introducer pin 292 extends through the cannula 512 and pierces the skin S of the user to insert the second cannula end 282 of the cannula 512 into the body of the user. With the cannula 512 inserted into the body of the user, the infusion unit 500 is in the installed state. With the infusion unit 500 installed, the needle hub is uncoupled from the infusion unit 500, which uncouples the introducer pin 292 from the infusion unit 500, leaving the infusion unit 500 coupled to the user. In the installed state, the infusion unit 500 provides a fluid flow path from the fluid reservoir associated with the fluid infusion device 102 (FIG. 1) into the body of the user.

Thus, the infusion unit 112, 500 provides for improved comfort for a user by providing a pivoting metal cannula with integral strain relief. In this regard, the use of the metal cannula 142, 512 having a blunt second cannula end 282 may reduce tissue inflammation as the metal cannula 142, 512 does not pierce the tissue when the infusion unit 112, 500 is subjected to an external force or load, and does not pierce the tissue when the metal cannula 142, 512 moves or pivots. In addition, the use of titanium, nickel-titanium or a titanium alloy for the metal cannula 142, 512 imparts flexibility to the metal cannula 142, 512 while maintaining a bend and kink resistance of the metal cannula 142, 512, which reduces tissue injury and inflammation and may result in longer wear life. The outer housing 130, 502 also distributes external forces and loads, such as compressive loads and shear impacts, over a larger area, which reduces user discomfort. Moreover, by being uncoupled from the movable needle mount 136 or the inner housing 506, the respective outer housing 130, 502 reduces a potential for the tube 110 detaching from the movable needle mount 136 or the inner housing 506 and improves user comfort as any pulling of the tube 110 results in pulling on the respective outer housing 130, 502 and not on the respective movable needle mount 136 or the inner housing 506. Further, the decoupled outer housing 130, 502 reduces a need for another adhesive layer to secure the respective inner housing 132 or inner housing 506 as any strain imparted to the tube 110 is distributed through the respective outer housing 130, 502. The use of the coupling device 140 having the adhesive layer 272 with the petals 276 also improves user comfort by reducing circumferential strain on curved portions of the user's body. In addition, the petals 276 reduce a potential for the adhesive layer 272 to peel off the user's body, as a peeling of one of the petals 276 would likely not result in a peeling off of the central portion 278 of the adhesive layer 272 since the peeling of one of the petals 276 would likely not propagate through the central portion 278. Thus, the adhesive layer 272 of the coupling device 140 reduces a likelihood of the infusion unit 112 being inadvertently uncoupled from the user.

In addition, it should be noted that while the outer housing 130, 502 has been described and illustrated herein as a substantially conical structure that surrounds the inner housing 132 and the inner housing 506, respectively, it should be understood that the outer housing 130, 502 may be configured in a number of different ways to provide strain relief to the infusion unit 112, 500. In one example, the outer housing may comprise a plurality of individual, separate or segmented "pie" pieces, which are positioned about the respective one of the inner housing 132 and the inner housing 506. Each of the segmented pie pieces would be de-coupled from the other segmented pie pieces and from the respective one of the inner housing 132 and the inner housing 506, enhancing overall site flexibility and comfort. In other example, instead of the outer housing, a thin adhesive patch spoke-like structure may be formed and used to adhere the tube 110 at multiple locations around the periphery of the inner housing 132 and the inner housing 506, which would also serve to protect the inner housing 132 and the inner housing 506 from strain or impacts.

Figure 15:
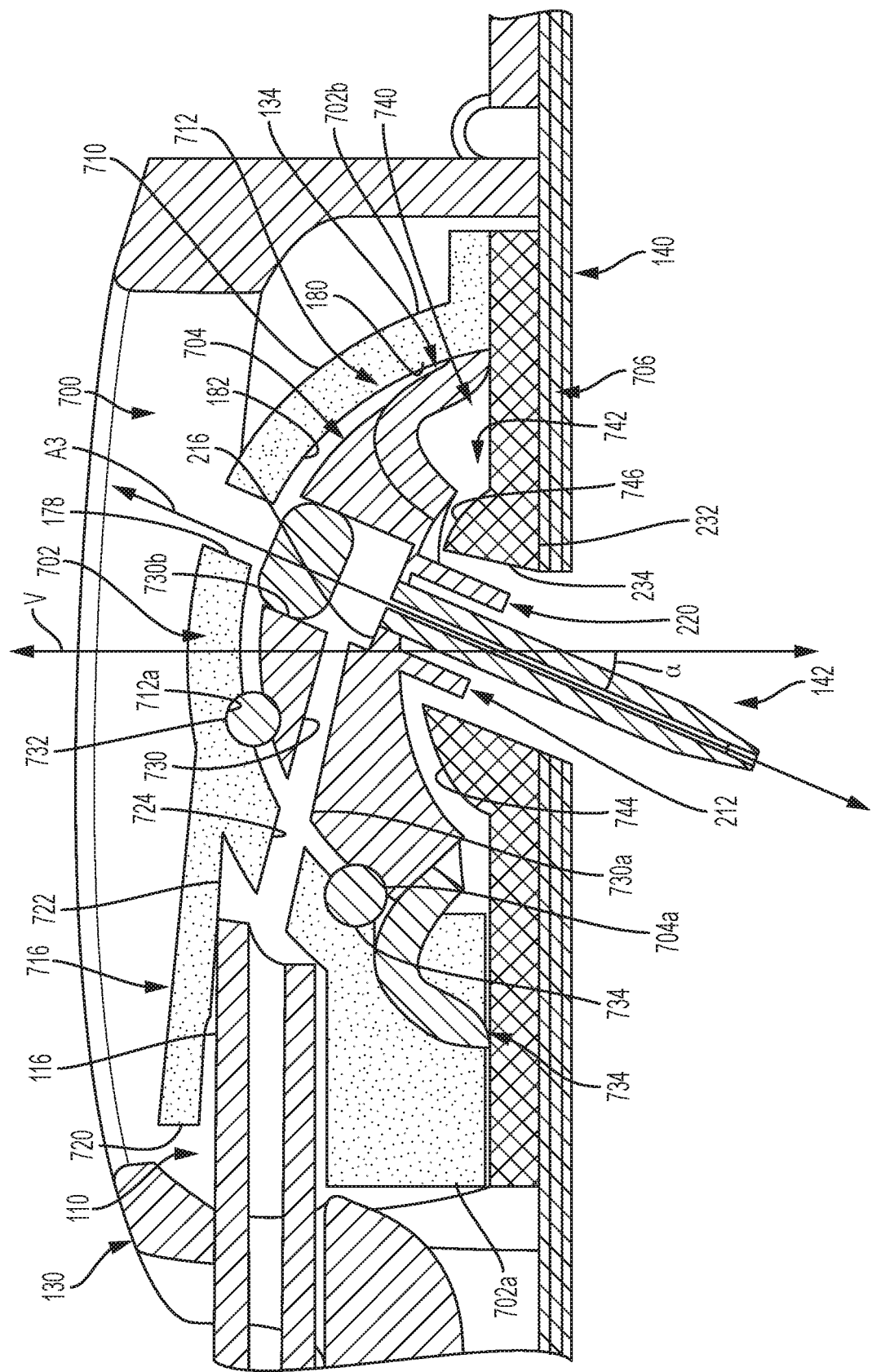
FIG. 15 is cross-sectional view of an exemplary infusion unit with a pivotable metal cannula and strain relief for use with the infusion set of FIG. 1.

It will be understood that the infusion unit 112 of the infusion set 104 described with regard to FIGS. 1-9 may be configured differently to provide a fluid flow path from the fluid infusion device 102 to the body of the user. In one example, with reference to FIG. 15, a cross-section of another exemplary infusion unit 700 for the infusion set 104 is shown. As the infusion unit 700 includes components that are substantially similar to or the same as the infusion unit 112 discussed with regard to FIGS. 1-9, the same reference numerals will be used to denote the same or similar features. The infusion unit 700 delivers fluid from the fluid reservoir associated with the fluid infusion device 102 (FIG. 1) received through the tube 110 into the body of the user. In one example, the infusion unit 700 includes the first or outer housing 130, a second or inner housing 702, the biasing member 134, an articulation member or movable needle mount 704, a mount 706, the coupling device 140 and the needle or metal cannula 142 (FIG. 3). In this example, the biasing member 134 and the movable needle mount 704 are received within a chamber defined between the inner housing 702 and the mount 706. It should be noted that while the infusion unit 700 is described herein as including the biasing member 134, the biasing member 134 may be optional.

The outer housing 130 surrounds the inner housing 702 and the mount 706, but is not coupled to the inner housing 702 or the mount 706. The inner housing 702 retains the biasing member 134 and the movable needle mount 704 on the mount 706. In one example, the inner housing 702 is composed of a polymer-based material, including, but not limited to, polypropylene, silicone or a thermoplastic elastomer. The inner housing 702 may be formed through molding, casting, printing, etc. The inner housing 702 is generally concave, however, the inner housing 702 may have any desired shape. The inner housing 702 includes an outer surface 710, an inner surface 712, the plurality of coupling slots 174, a tube receiving portion 716 and the needle bore 178.

The outer surface 710 is substantially smooth, and is substantially conical. The inner surface 712 is opposite the outer surface 710. The inner surface 712 includes the biasing member clearance surface 180 and the first articulation surface 182. The first articulation surface 182 is spherical and concave. The first articulation surface 182 is defined on the inner surface 712 so as to be offset from a central axis of the inner housing 702. In this example, the first articulation surface 182 is offset from the central axis toward a second end 702b of the inner housing 702. Generally, the first articulation surface 182 extends from a first side of the inner surface 712 to a second, opposite side of the inner surface 712 near or adjacent to the second end 702b of the inner housing 702. The first articulation surface 182 cooperates with the movable needle mount 704 to enable the cannula 142 to move or pivot relative to the angle α defined between the central vertical axis V of the infusion unit 700 and an axis A3 through a center line of the cannula 142. In one example, the movable needle mount 704 is movable or pivotable the angle β relative to the angle α.

The tube receiving portion 716 is substantially cylindrical, and is sized to receive the first end 116 of the tube 110 and to cooperate with the tube 110 to define the fluid flow path to the user. The tube receiving portion 716 is defined at a first end 702a of the inner housing 702. The tube receiving portion 716 includes a first end 720 and an opposite second end 722. The first end 720 receives a portion of the tube 110 adjacent to the first end 116. The second end 722 is fixedly coupled to the first end 116 of the tube 110, and includes an outlet 724. Generally, the first end 116 of the tube 110 is fixedly coupled to the second end 722 via any suitable technique, including, but not limited to, adhesives, ultrasonic welding, etc. The outlet 724 defines a fluid flow path from the first end 116 of the tube 110 into the movable needle mount 704. The outlet 724 is in fluid communication with the movable needle mount 704 to direct the fluid from the fluid reservoir of the fluid infusion device 102 into the body of the user.

The movable needle mount 704 enables the cannula 142 to move or pivot relative to the inner housing 702, and thus, the infusion unit 700. In one example, the movable needle mount 704 enables the cannula 142 to move or pivot when the skin S (FIG. 2) of the user moves or when an external force or load is applied to the infusion unit 700. In one example, the movable needle mount 704 is composed of a polymer-based material, including, but not limited to, polypropylene, silicone or a thermoplastic elastomer. The movable needle mount 704 may be formed through molding, casting, printing, etc. In one example, the movable needle mount 704 includes the needle guide 202, the septum 204, the septum bore 206, the second articulation surface 208, the ledge 224, a fluid conduit 730 and at least one sealing member 732. In one example, the movable needle mount 704 is substantially conical, but the movable needle mount 704 may have any desired shape.

The fluid conduit 730 fluidly couples the movable needle mount 704 to the inner housing 702. In one example, the fluid conduit 730 is defined through the movable needle mount 704 from a first end 704a of the movable needle mount 704 to inlet 216 of the needle guide 202. The fluid conduit 730 is cylindrical; however, the fluid conduit 730 may have any desired shape. The fluid conduit 730 includes a conduit inlet 730a at the first end 704a, and a conduit outlet 730b. The conduit inlet 730a is fluidly coupled to the outlet 724 of the inner housing 702, and the conduit outlet 730*b* is fluidly coupled to the inlet 216 of the needle guide 202 to enable fluid to flow from the first end 116 of the tube 110 through the inner housing 702, the movable needle mount 704 and into the cannula 142.

The at least one sealing member 732 substantially surrounds the conduit inlet 730*a*. In one example, the at least one sealing member 732 is a single sealing member; however, multiple sealing members may be employed. In this example, the sealing member 732 ensures that the fluid from the tube 110 enters the fluid conduit 730. The sealing member 732 is substantially annular. The sealing member 732 is retained between the inner housing 702 and the movable needle mount 704. In one example, the sealing member 732 may be fixedly coupled to the inner surface 712 of the inner housing 702, via adhesives, ultrasonic welding, etc. In this example, the inner surface 712 may define an annular recess 712*a*, which may at least partially receive the sealing member 732 and the sealing member 732 may be fixedly coupled to the annular recess 712*a*. The sealing member 732 is generally composed of a biocompatible polymer-based material, including, but not limited to, an elastomer, silicone, etc. In one example, the sealing member 732 includes a central member bore 734. The central member bore 734 is circular, and is sized to surround the conduit inlet 730*a*. The sealing member 732 enables the movable needle mount 704 to move while inhibiting the egress of fluid.

The mount 706 is coupled to the coupling device 140 and to the inner housing 702. The mount 706 is substantially circular; however, the mount 706 may have any desired shape. In one example, the mount 706 is composed of a polymer-based material, including, but not limited to, polypropylene, silicone or a thermoplastic elastomer. The mount 706 may be formed through molding, casting, printing, etc. The mount 706 includes a first mount surface 740, the second mount surface 232 opposite the first mount surface 230 and the central mount bore 234. The first mount surface 740 includes the plurality of projections 240, the plurality of snap fingers 242 and a needle mount interface 742. It should be noted in that in alternative embodiments, the first mount surface 740 may include other features that enable the mount 706 to be coupled to the inner housing 702, via ultrasonic welding or adhesives, instead of a snap-fit via the plurality of snap fingers 242, for example.

The needle mount interface 742 cooperates with the movable needle mount 704 to limit an amount of movement or rotation of the movable needle mount 704. In one example, the needle mount interface 742 includes a first concave surface 744 and a second concave surface 746. The first concave surface 744 provides a stop or contact surface for the movable needle mount 704, which limits a movement or rotation of the movable needle mount 704. In one example, the first concave surface 744 has a curvature that is shaped to cooperate with an outer surface of the movable needle mount 704. It should be noted, however, that the first concave surface 744 may have any desired shape to provide a stop for a movement of the movable needle mount 704. The second concave surface 746 has a shape that is configured to match an exterior surface of the annular guide 220 of the movable needle mount 704. The second concave surface 746 limits a further advancement or movement of the cannula 142, for example, when the inner housing 702 is compressed by an external force. In the example of a compression of the inner housing 702 by the external force, an exterior surface of the annular guide 220 contacts the second concave surface 746.

As the assembly of the infusion unit 700 is substantially the same as the assembly of the infusion unit 112 discussed with regard to FIGS. 1-9, only the differences between the assembly of the infusion unit 112 and the infusion unit 700 will be discussed in detail herein. Generally, in order to assemble the infusion unit 700 and couple the tube 110 to the infusion unit 700, in one example, with the movable needle mount 704 formed, the movable needle mount 704 is positioned onto the biasing member 134. With the inner housing 132 formed, the first end 116 of the tube 110 is fixedly coupled to the tube receiving portion 716 of the inner housing 702. Generally, prior to fixedly coupling the tube 110 to the inner housing 702, the connector assembly 114 is coupled to the second end 118 of the tube 110. With the tube 110 attached, the inner housing 702 is snapped into the mount 706 such that the movable needle mount 704 and the biasing member 134 are sandwiched between the mount 706 and the inner housing 702 and a portion of the tube 110 extends through the clearance aperture 176. With the outer housing 130 formed, the outer housing 130 is positioned about the inner housing 132 and a portion of the tube 110 is received within the retaining recess 166 such that the portion of the tube 110 extends substantially about a circumference of the outer housing 130 near the perimeter of the outer housing 130. With the coupling device 140 formed, the mounting layer 270 is fixedly coupled to the second mount surface 232 and the surface 162*b* of each base 162 of the retaining flanges 148. The tube 110 may be coupled to the infusion unit 700 with the in-line connector 110*b* and the connector assembly 114 coupled to the tube 110 such that once the tube 110 is coupled to the assembled infusion unit 700, the infusion set 104 is formed.

As the installation of the infusion unit 700 on the user is substantially the same as the installation of the infusion unit 112 on the user discussed with regard to FIGS. 1-9, the installation of the infusion unit 700 will not be discussed in detail herein.

Figure 16:
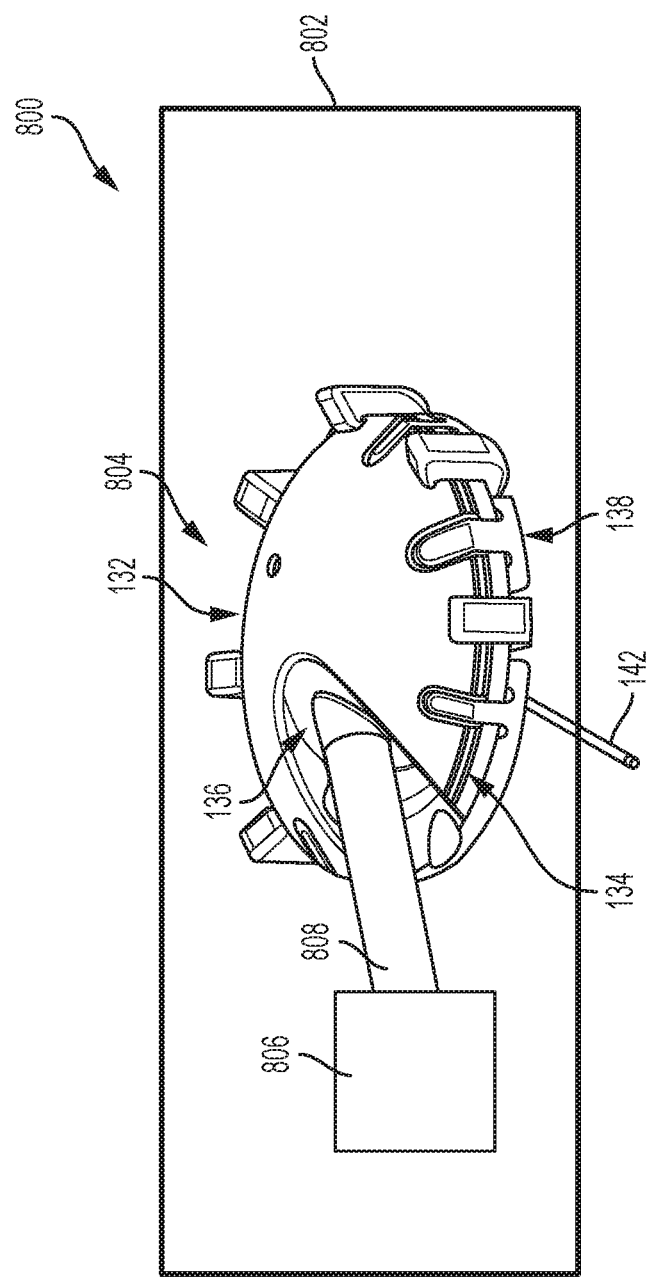
FIG. 16 is a schematic view of an exemplary embodiment of a fluid infusion device including an infusion unit with a pivotable metal cannula according to various teachings of the present disclosure.

It will be understood that the fluid infusion system 100 described with regard to FIGS. 1-15 may be configured differently to provide a fluid flow path from a fluid reservoir to the body of the user. In one example, with reference to FIG. 16, a fluid infusion system 800 is shown. The fluid infusion system 800 includes two main components: a fluid infusion device 802 (e.g., an insulin patch pump) and an infusion unit 804, which is disposed within and fluidly coupled to the fluid infusion device 802. Thus, in this example, the fluid infusion device 802 and the infusion unit 804 are coupled to the body of the user. In this example, the fluid infusion device 802 accommodates an internal fluid reservoir 806 for the fluid to be delivered to the user. A tube 808 represents the fluid flow path that couples the fluid reservoir 806 to the infusion unit 804. When installed as depicted in FIG. 16, the tube 808 extends internally from the fluid reservoir 806 to the internal infusion unit 804, which in turn provides a fluid pathway to the body of the user through the cannula 142.

The infusion unit 804 delivers fluid from the fluid reservoir 806 associated with the fluid infusion device 802 received through the tube 808 into the body of the user. As the infusion unit 804 includes components that are substantially similar to or the same as the infusion unit 112 discussed with regard to FIGS. 1-9, the same reference numerals will be used to denote the same or similar features. In the example, the infusion unit 804 includes the second or inner housing 132, the biasing member 134, the articulation member or movable needle mount 136, the mount 138 and the needle or metal cannula 142. It should be noted that while the infusion unit 112 is described herein as including the biasing member 134, the biasing member 134 may be optional. The infusion unit 804 provides a fluid flow path from the fluid reservoir 806 to the body of the user via the cannula 142, which is movable relative to the fluid infusion device 802.

Thus, the infusion unit 804 associated with the fluid infusion device 802 provides for the pivotable metal cannula 142, which has a blunt second cannula end 282 may reduce tissue inflammation as the metal cannula 142 does not pierce the tissue when the infusion unit 804 and/or the fluid infusion device 802 is subjected to an external force or load, and does not pierce the tissue when the metal cannula 142 moves or pivots. In addition, the use of titanium, nickel-titanium or a titanium alloy for the metal cannula 142 imparts flexibility to the metal cannula 142 of the infusion unit 804 while maintaining a bend and kink resistance of the metal cannula 142, which reduces tissue injury and inflammation and may result in longer wear life.

It will be understood that the fluid infusion system 100 described with regard to FIGS. 1-15 may be configured differently to provide a fluid flow path from a fluid reservoir to the body of the user. In one example, with reference to FIG. 16A, a fluid infusion system 900 is shown. The fluid infusion system 900 includes two main components: a fluid infusion device 902 (e.g., an insulin patch pump) and an infusion unit 904, which is disposed within and fluidly coupled to the fluid infusion device 902. Thus, in this example, the fluid infusion device 902 and the infusion unit 904 are coupled to the body of the user. In this example, the fluid infusion device 902 accommodates an internal fluid reservoir 906 for the fluid to be delivered to the user. A tube 908 represents the fluid flow path that couples the fluid reservoir 906 to the infusion unit 904. When installed as depicted in FIG. 16A, the tube 908 extends internally from the fluid reservoir 906 to the internal infusion unit 904, which in turn provides a fluid pathway to the body of the user through the cannula 512.

The infusion unit 904 delivers fluid from the fluid reservoir 906 associated with the fluid infusion device 902 received through the tube 908 into the body of the user. As the infusion unit 904 includes components that are substantially similar to or the same as the infusion unit 500 discussed with regard to FIGS. 10-14, the same reference numerals will be used to denote the same or similar features. In the example, the infusion unit 904 includes the second or inner housing 506, the mount 508 and the needle or metal cannula 512. The infusion unit 904 provides a fluid flow path from the fluid reservoir 906 to the body of the user via the cannula 512, which is movable relative to the fluid infusion device 902.

Thus, the infusion unit 904 associated with the fluid infusion device 902 provides for the pivotable metal cannula 512, which has a blunt second cannula end 282 may reduce tissue inflammation as the metal cannula 512 does not pierce the tissue when the infusion unit 904 and/or the fluid infusion device 902 is subjected to an external force or load, and does not pierce the tissue when the metal cannula 512 moves or pivots. In addition, the use of titanium, nickel-titanium or a titanium alloy for the metal cannula 512 imparts flexibility to the metal cannula 512 of the infusion unit 904 while maintaining a bend and kink resistance of the metal cannula 512, which reduces tissue injury and inflammation and may result in longer wear life.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An infusion set for use with a fluid infusion device having a fluid reservoir, the infusion set comprising:
    a cannula that provides a fluid flow path;
    an inner housing including an articulation member coupled to the cannula, the articulation member pivotable relative to the inner housing to move the cannula relative to the inner housing, and the inner housing is coupled to a fluid supply line to provide a fluid to the cannula, the fluid supply line to be coupled to the fluid reservoir to receive the fluid;
    an outer housing uncoupled from the inner housing that surrounds the inner housing and receives a portion of the fluid supply line; and
    a coupling device to removably couple the infusion set to an anatomy, the coupling device including a mounting layer and an adhesive layer, the mounting layer extends over the adhesive layer and is coupled to the inner housing and the outer housing, and the adhesive layer includes a plurality of petals that extend radially outward from a central portion.

2. The infusion set of claim 1, wherein the cannula is coupled to the articulation member so as to extend along an axis that is substantially transverse to a vertical axis that extends through the infusion set, and the articulation member moves the cannula about the axis.

3. The infusion set of claim 1, wherein the inner housing includes a first articulation surface and the articulation member is a movable needle mount received within the inner housing and having a second articulation surface that cooperates with the first articulation surface to move the cannula.

4. The infusion set of claim 3, further comprising a biasing member that contacts at least a portion of the movable needle mount and applies a force to the movable needle mount to return the movable needle mount to a neutral position.

5. The infusion set of claim 1, further comprising a mount coupled to the inner housing, and the articulation member is coupled between the inner housing and the mount.

6. The infusion set of claim 1, wherein the articulation member is a spherical ball.

7. The infusion set of claim 1, wherein the cannula is composed of a metal or metal alloy and includes a blunt tip.

8. The infusion set of claim 7, wherein the blunt tip of the cannula includes a slot.

9. The infusion set of claim 1, wherein the fluid infusion device is an insulin infusion device, and the cannula of the infusion set is in fluid communication with the fluid reservoir associated with the insulin infusion device through the fluid supply line.

10. The infusion set of claim 1, wherein the outer housing includes a plurality of retaining flanges that cooperate to receive the portion of the fluid supply line such that the portion of the fluid supply line is positioned about at least a portion of a circumference of the outer housing and each petal of the plurality of petals of the adhesive layer is associated with a respective one of the plurality of retaining flanges.

11. An infusion set for use with a fluid infusion device having a fluid reservoir, the infusion set comprising:
- a cannula that provides a fluid flow path;
- an inner housing including an articulation member coupled to the cannula, the articulation member pivotable relative to the inner housing to move the cannula relative to the inner housing, and the inner housing is coupled to a fluid supply line to provide a fluid to the cannula, the fluid supply line to be coupled to the fluid reservoir to receive the fluid;
- an outer housing uncoupled from the inner housing that surrounds the inner housing, the outer housing having a plurality of retaining flanges that cooperate to receive a portion of the fluid supply line such that the portion of the fluid supply line is positioned about a circumference of the outer housing; and
- a coupling device to removably couple the infusion set to an anatomy, the coupling device including a mounting layer and an adhesive layer, the mounting layer extends over the adhesive layer and is coupled to the inner housing and the outer housing, the mounting layer and the adhesive layer including a respective plurality of petals that extend radially outward from a central portion, with each petal of the plurality of petals associated with a respective one of the plurality of retaining flanges.

12. The infusion set of claim 11, wherein the inner housing includes a first articulation surface and the articulation member is a movable needle mount received within the inner housing and having a second articulation surface that cooperates with the first articulation surface to move the cannula.

13. The infusion set of claim 12, further comprising a biasing member that contacts at least a portion of the movable needle mount and applies a force to the movable needle mount to return the movable needle mount to a neutral position.

14. The infusion set of claim 13, further comprising a mount coupled to the inner housing, and the articulation member is coupled between the inner housing and the mount.

15. The infusion set of claim 11, wherein the articulation member is a spherical ball.

16. An infusion set for use with a fluid infusion device having a fluid reservoir, the infusion set comprising:
- a metal cannula that provides a fluid flow path;
- an inner housing including an articulation member coupled to the cannula, the articulation member pivotable relative to the inner housing to move the cannula relative to the inner housing, and the inner housing is coupled to a fluid supply line to provide a fluid to the cannula, the fluid supply line to be coupled to the fluid reservoir to receive the fluid;
- an outer housing uncoupled from the inner housing that surrounds the inner housing, the outer housing having a plurality of retaining flanges that cooperate to receive a portion of the fluid supply line such that the portion of the fluid supply line is positioned about a circumference of the outer housing; and
- a coupling device to removably couple the infusion set to an anatomy, the coupling device including an adhesive layer having a plurality of petals that extend radially outward from a central portion, with each petal of the plurality of petals associated with a respective one of the plurality of retaining flanges,
- wherein the inner housing and the outer housing are each coupled to the coupling device.

* * * * *